US012674797B2

(12) United States Patent
Klein et al.

(10) Patent No.: US 12,674,797 B2
(45) Date of Patent: Jul. 7, 2026

(54) METHOD FOR MEASURING NUCLEIC ACID CONTENT IN LIPID NANOPARTICLES USING ULTRAVIOLET SPECTROMETRY

(71) Applicant: Merck Sharp & Dohme LLC, Rahway, NJ (US)

(72) Inventors: Lee J. Klein, Collegeville, PA (US); Leia C. Epstein, Norristown, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1144 days.

(21) Appl. No.: 17/762,210

(22) PCT Filed: Sep. 22, 2020

(86) PCT No.: PCT/US2020/051904
§ 371 (c)(1),
(2) Date: Mar. 21, 2022

(87) PCT Pub. No.: WO2021/061594
PCT Pub. Date: Apr. 1, 2021

(65) Prior Publication Data

US 2022/0397570 A1 Dec. 15, 2022

Related U.S. Application Data

(60) Provisional application No. 62/907,103, filed on Sep. 27, 2019.

(51) Int. Cl.

| | |
|---|---|
| ***G01N 33/52*** | (2006.01) |
| ***A61K 9/1271*** | (2025.01) |
| ***G01N 21/33*** | (2006.01) |

(52) U.S. Cl.
CPC .......... *G01N 33/52* (2013.01); *A61K 9/1271* (2013.01); *G01N 21/33* (2013.01)

(58) Field of Classification Search
None
See application file for complete search history.

(56) References Cited

U.S. PATENT DOCUMENTS

2012/0276209 A1 11/2012 Cullis et al.
2013/0245107 A1* 9/2013 de Fougerolles .... A61K 9/1272 514/44 R (Continued)

FOREIGN PATENT DOCUMENTS

WO 2017070622 A1 4/2017
WO WO-2018089540 A1 * 5/2018 .......... A61K 9/5123
WO 2018170260 A1 9/2018

OTHER PUBLICATIONS

IDT, Oligo quantification—getting it right, published Dec. 14, 2016, https://www.idtdna.com/pages/education/decoded/article/oligo-quantification-getting-it-right (Year: 2016).*

(Continued)

*Primary Examiner* — Maris R Kessel
*Assistant Examiner* — Mickey Huang
(74) *Attorney, Agent, or Firm* — John David Reilly; John C. Todaro

(57) ABSTRACT

An ultraviolet (UV) absorbance assay for measuring the concentration of large RNA molecules such as mRNA in suspensions comprising RNA-lipid nanoparticles (RNA-LNPs) is described.

20 Claims, 13 Drawing Sheets

Specification includes a Sequence Listing.

(56) References Cited

U.S. PATENT DOCUMENTS

| | | | | |
|---|---|---|---|---|
| 2013/0332084 A1* | 12/2013 | Boonefaes | G01N 21/33 | 702/19 |
| 2017/0196809 A1* | 7/2017 | Bowman | C12N 15/113 | |

OTHER PUBLICATIONS

Anastassia Kanavarioti, HPLC methods for purity evaluation of man-made single-stranded RNAs, Jan. 31, 2019, Scientific Reports, (2019) 9:1019 (Year: 2019).*

Matsuzaki et al., Optical characterization of liposomes by right angle light scattering and turbidity measurement, Biochimica et Biophysica Acta (BBA)—Biomembranes, vol. 1467, Issue 1, Jul. 31, 2000, pp. 219-226 (Year: 2000).*

Sylwia Studzińska and Bogusław Buszewski, Evaluation of ultrahigh-performance liquid chromatography columns for the analysis of unmodified and antisense oligonucleotides, Anal Bioanal Chem. Jun. 18, 2014;406(28):7127-7136. (Year: 2014).*

Li et al., Alkylamine ion-pairing reagents and the chromatographic separation of oligonucleotides, Dec. 14, 2018, Journal of Chromatography A, vol. 1580, Dec. 14, 2018, pp. 110-119 (Year: 2018).*

Aranda IV, Roman et al., Comparison and evaluation of RNA quantification methods using viral, prokaryotic, and eukaryotic RNA over a 10(4) concentration range, Analytical Biochemistry, 2009, 122-127, 387.

Hashimoto, J.G. et al., Comparison of RiboGreen and 18S rRNA quantitation for normalizing real-time RT-PCR expression analysis, BioTechniques, 2004, 54-60, 36(1).

Integrated DNA Technologies. Oligo quantification—getting it right. Jan. 18, 2013 [online] [retrieved Jan. 19, 2021]. Available on the internet: URL: https ://www. idtdna.com/pages/education/decoded/article/oligo-quantification-getting-it-right. Especially PDF p. 2 para 2-3, PDF p. 3 para 3. (4 pages).

Jayaraman, Muthusamy et al., Maximizing the Potency of siRNA Lipid Nanoparticles for Hepatic Gene Silencing In Vivo, Angew. Chem. Int. Ed., 2012, 8529-8533, 51.

Sabnis, Staci et al., A Novel Amino Lipid Series for mRNA Delivery: Improved Endosomal Escape and Sustained Pharmacology and Safety in Non-human Primates, Molec. Thera., 2018, 1509-1519, 26.

Taoka, M. et al., An analytical platform for mass spectrometry-based identification and chemical analysis of RNA in ribonucleoprotein complexes, Nucleic Acids Research, 2009, 1-14, 37(21):e140.

* cited by examiner

SEQUENCE LISTING

```
<160> NUMBER OF SEQ ID NOS: 1

<210> SEQ ID NO 1
<211> LENGTH: 1884
<212> TYPE: RNA
<213> ORGANISM: Artificial Sequence
<220> FEATURE:
<223> OTHER INFORMATION: Sample mRNA sequence

<400> SEQUENCE: 1

gggaaauaag agagaaaaga agaguaagaa gaaauauaag agcauggaac ugcucauuuu      60

gaaggcaaac gcuaucacga caauacucac ugcagugacc uucuguuuug ccucaggcca     120

gaacauaacc gaggaguuuu aucaaucuac augcagcgcu guaucuaaag gcuaccugag     180

ugcgcuccgc acaggauggu acaccuccgu gaucaccauc gagcucagca auauuaaaga     240

gaacaagugc aaugguaccg acgcuaaagu caaacuuauc aagcaggaac ucgacaaaua     300

uaagaacgcu gugaccgagc ugcaguuauu gaugcagagu acaccugcca ccaauaacag     360

agcuaggagg gaguugccua gguuuaugaa cuacacucuc aacaacgcga agaaaaccaa     420

ugugacgcua uccaagaaac ggaagaggag guuccugggg uuucuuuuag gggugggcuc     480

ugccauugcu uccggcgugg cuguauguaa aguucuccac cucgagggag agguuaauaa     540

gauuaagucg gcccugcuga guacuaacaa agcaguggug ucgcugagua acggaguaag     600

uguguuaaca uuuaaggugc uggaccucaa gaauuauauu gacaaacagu ugcuuccuau     660

ucuaaacaaa cagagcuguu caauaaguaa uauugaaacu guuauugagu uucagcagaa     720

gaacaacagg cuucuugaga uuacacgcga guucaguguc aaugccggcg uuacaacacc     780

cgugucuacc uacaugcuga cgaauucuga gcuucucucu cucauaaacg acaugcccau     840

uacgaaugac caaaagaaac uuauguccaa caacgugcag auugugcgac agcaauccua     900

uagcauuaug uguaucauca aggaagaggu acucgcuuau guugugcagc uaccacucua     960
```

-continued

```
uggugugauu gacacccccu guuggaagcu gcauaccagu ccacucugca ccacuaacac   1020

aaaggaaggg agcaauauuu gccucacucg aaccgacagg gggugguauu gcgauaaugc   1080

gggcuccgug uccuucuuuc cacaggcuga aacuuguaag guacagucaa accgcguguu   1140

cugugauacu augaauucuc ugacucuucc cagcgagguu aaucucugca acgucgacau   1200

uuucaauccu aaauaugacu gcaagaucau gaccagcaag accgacgucu ccagcucagu   1260

aaucacuagc cuaggggcca uuguaagcug cuauggcaaa accaagugua cugccucuaa   1320

uaagaacaga ggcauaauua aaaccuuuuc aaauggcugu gacuaugugu cgaauaaggg   1380

cgucgacacg gucucaguag ggaauacccu cuacuacguu aacaaacagg aaggcaaauc   1440

ccuuuaugua aagggcgagc ccaucauaaa uuucuacgac ccacuugugu uccccaguga   1500

ugaauucgau gcaucaaucu cccaggugaa cgaaaagauc aaucaauccc uugcuuuuau   1560

acgaaaguca gaugaacucc ugcauaacgu gaaugcuggg aaaucuacaa ccaacaucau   1620

gaucacuacc aucauuauug ugauuaucgu aauucugcua uccuugauug cugucgggcu   1680

gcuucuguac uguaaggcca gaucgacgcc ugugacccuu ucaaaagacc aacuuagcgg   1740

uaucaauaau auugccuuua gcaauugaua auaggcugga gccucggugg ccaugcuucu   1800

ugccccuugg gccucccccc agccccuccu ccccuuccug cacccguacc cccguggucu   1860

uugaauaaag ucugaguggg cggc                                          1884
```

METHOD FOR MEASURING NUCLEIC ACID CONTENT IN LIPID NANOPARTICLES USING ULTRAVIOLET SPECTROMETRY

CROSS-REFERENCE TO RELATED APPLICATIONS

This application is a National Stage application of International Patent Application No. PCT/US2020/051904, filed Sep. 22, 2020, which claims priority to U.S. Provisional Patent Application No. 62/907,103, filed Sep. 27, 2019.

BACKGROUND OF THE INVENTION

(1) Field of the Invention

The present invention relates to an ultraviolet (UV) absorbance assay for measuring the concentration of ribonucleic acid (RNA) molecules in suspensions comprising RNA-lipid nanoparticles (RNA-LNPs). In particular, wherein the RNA-LNPs comprise mRNA.

(2) Description of Related Art

UV spectrometry and Inductively-Coupled Plasma Optical Emission Spectrometry (ICP) are analytical methods generally used to accurately determine the mRNA content in solutions. However, the analysis is quite complicated due to the appearance of manifold secondary structures in solution, which are affected by temperature, pH, solvents, and other factors. Lipid nanoparticles (LNPs), formulated as a carrier for mRNA adds additional complication for the analysis.

The advantages of ICP are its high reproducibility, insensitivity to RNA quality, and insensitivity to the solvent, including solvent pH. However, analysis by ICP is much more costly than by other methods owing to expense of owning and operating the equipment and because relatively large volumes of sample are required for the analysis. Additionally, it is an indirect measurement of RNA and possible phosphate contamination via DNA, lipids, or buffer components makes it impractical for most laboratories. Aranda I V et al., Analytical Biochemistry 387: 122-127 (2009) provides a comparison of RNA measurement methods in common use.

UV absorbance measurement is a relatively convenient analytical method for measuring RNA content having the advantages of being an assay that can be performed rapidly using small volumes and having a linear relationship between UV absorbance and concentration of RNA. However, to get a robust and reproducible UV absorbance measurement of RNA content in a sample suspension of LNPs containing the RNA, the RNA-LNPs must be completely disrupted, the RNA must be completely denatured, and the method reagents and conditions must provide for optical transparency above 240 nm to enable measurement of the RNA absorbance. The UV spectrum of a sample containing partially or even completely denatured LNP and mRNA may be altered by the presence of the strongly complexing cationic lipids that comprise the LNP and which constitutes a majority of the LNP by weight. Thus, the RNA should also be free of bound lipids.

While there are many methods for disrupting RNA-LNPs and completely denaturing RNA without absorbing above 240 nm, there is no method that completely dissociates the RNA from the cationic lipids comprising the LNP that are amenable to use of UV spectroscopy to measure mRNA content in LNPs.

BRIEF SUMMARY OF THE INVENTION

The present invention provides a method for measuring RNA content of a suspension of RNA-LNPs in which the LNPs comprise ionizable cationic lipids. The method comprises disrupting the RNA-LNPs, completely denaturing the RNA, and displacing the ionizable cationic lipids bound or associated with the RNA at ambient temperatures using reagents that are optically transparent above 240 nm and which maintain the RNA completely denatured and not bound to ionizable cationic lipids for a time sufficient to allow the absorbance of the RNA to be measured at the lambda maximum of the RNA ($\lambda_{max}$). The invention is founded on the discovery that adding a diluent comprising a surfactant and an alkylamine to a suspension of RNA-LNPs will result in a solution wherein the surfactant disrupts the RNA-LNPs into its RNA and LNP components and the alkylamine raises the pH of the solution to about pH 11 to about pH 12 or a pH of at least pH 12 to denature the RNA and further displaces the ionizable cationic lipids associated with or complexed to the denatured RNA. The resulting solution is sufficiently transparent to allow for direct determination of RNA content by measuring absorbance at lambda maximum of the RNA ($\lambda_{max}$). The present invention is particularly useful for measuring mRNA content in RNA-LNPs comprising the mRNA.

Thus, the present invention provides a method for measuring the RNA concentration of a suspension of RNA-LNPs wherein the RNA-LNPs comprise ionizable cationic lipids, the method comprising: (a) mixing a suspension of RNA-LNPs with an assay diluent comprising a surfactant and an alkylamine to provide a diluted sample solution; (b) measuring absorbance of the diluted sample solution at lambda maximum of the RNA ($\lambda_{max}$) to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (c) using the Net Absorbance or the adjusted Net Absorbance to determine the RNA concentration in the suspension of the RNA-LNPs.

In a further embodiment, a method is provided for measuring the RNA concentration of a suspension of RNA-LNPs, the method comprising (a) providing a predetermined or premeasured volume of a sample suspension comprising RNA-LNPs wherein the RNA-LNPs comprise ionizable cationic lipids; (b) mixing the sample suspension of RNA-LNPs with a predetermined volume of an assay diluent comprising a surfactant and an alkylamine to provide a diluted sample solution in which the RNA is denatured and dissociated from or not bound to the ionizable cationic lipids; (c) measuring absorbance of the diluted sample solution at $\lambda_{max}$ in the diluted sample solution to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (d) using the Net Absorbance or the adjusted Net Absorbance to determine the RNA concentration in the suspension of the RNA-LNPs.

In a further aspects of the above embodiments, the RNA concentration is determined using the formula $$mRNA\left(\frac{\text{mg}}{\text{mL}}\right) = \left(\frac{\text{Net Absorbance or adjusted Net Absorbance}}{\text{path length (cm)}}\right) \times$$

-continued $$\left(40\ \frac{\mu g \cdot cm}{mL}\right) \times \left(\frac{1\ \frac{mg}{mL}}{1000\ \frac{\mu g}{mL}}\right) \times \text{Dilution Factor}$$

wherein $$\text{Dilution Factor} = \frac{\text{Diluted Sample Solution volume } (\mu L)}{\text{Initial Sample Suspension volume } (\mu L)}$$

and adjusted Net Absorbance=absorbance at $\lambda_{max}$−absorbance at 400 nm.

In general, the alkylamine selected is (i) an alkylamine that when added to the sample suspension results in a diluted sample solution having a pH that is at least pH 11 or a pH of about pH 12 or a pH of at least pH 12 and (ii) capable of displacing ionizable cationic lipids from the RNA. In further embodiments, the alkylamine comprises a tertiary amine of the formula NRR'R" wherein R, R', and R" are each independently a C1 to C18 alkyl. In a further embodiment, the alkylamine is selected from the group consisting of N,N-dimethylbutylamine (DMBA; CAS 927-62-8), N,N-diethylethanamine (TEA; CAS 121-44-8), N,N-diisopropylethylamine (DIPEA; CAS 7087-68-5), and hexan-1-amine (1-HA; CAS 111-26-2).

In general, the surfactant selected is capable of disrupting or dissociating RNA-LNP complexes into its RNA and lipid components. In particular embodiments, the surfactant is selected from the group consisting of sodium dodecyl sulfate (SDS; CAS 151-21-3), cetyltrimethylammonium bromide (C-TAB; CAS 57-09-0), and polyethylene glycol alkyl ether (BRIJ®, a registered trademark of Croda International PLC). In a particular embodiment, the surfactant is SDS and the alkylamine is DMBA or the surfactant is a polyethylene glycol alkyl ether and the alkylamine is 1-HA. In a further embodiment, the surfactant is polyethylene glycol hexadecyl ether (CAS 9004-95-9; BRIJ®-58) and the alkylamine is 1-HA wherein the polyethylene glycol hexadecyl ether has the formula $HO—(CH_2CH_2O)_{20}—(CH_2)_{15}—CH_3$ (also known as.

In particular aspects of the above embodiments of the method, the ionizable cationic lipids comprise a tertiary amine. In a further embodiment, the ionizable cationic lipid comprises a tertiary amine and at least one saturated or unsaturated hydrocarbon chain comprising at least nine carbon atoms. In a particular embodiment, the ionizable cationic lipid is dilinoleylmethyl-4-dimethylaminobutyrate (D-Lin-MC3-DMA; CAS 1224606-06-7).

In a particular aspects of the above embodiments of the method, the assay diluent further includes a metal chelator, which in a further embodiment may be ethylenediaminetetraacetic acid (EDTA).

In particular aspects of the above embodiments of the method, the assay diluent comprises about 750 mM N,N-dimethylbutylamine, about 10% w/v SDS, and about 1 mM EDTA.

In a further embodiment, the present invention provides a method for measuring the ribonucleic acid (RNA) concentration of a suspension of RNA-lipid nanoparticle (RNA-LNPs) wherein the RNA-LNPs comprise ionizable cationic lipids, the method comprising: (a) mixing a suspension of RNA-LNPs with an assay diluent comprising sodium dodecyl sulfate (SDS; CAS 151-21-3) and N,N-dimethylbutylamine (DMBA; CAS 927-62-8) to provide a diluted sample solution; (b) measuring absorbance of the diluted sample solution at lambda maximum of the RNA ($\lambda_{max}$) to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (c) using the Net Absorbance or the adjusted Net Absorbance to determine the RNA concentration in the suspension of the RNA-LNPs.

In a further still embodiment, the present invention provides a method for measuring the ribonucleic acid (RNA) concentration of a suspension of RNA-lipid nanoparticle (RNA-LNPs) wherein the RNA-LNPs comprise ionizable cationic lipids, the method comprising: (a) mixing a suspension of RNA-LNPs with an assay diluent comprising polyethylene glycol hexadecyl ether (CAS 9004-95-9) and hexan-1-amine (1-HA; CAS 111-26-2) to provide a diluted sample solution; (b) measuring absorbance of the diluted sample solution at lambda maximum of the RNA ($\lambda_{max}$) to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (c) using the Net Absorbance or the adjusted Net Absorbance to determine the RNA concentration in the suspension of the RNA-LNPs.

In particular aspects of the above embodiments, the ionizable cationic lipids comprise a tertiary amine. In a further embodiment, the ionizable cationic lipid comprises a tertiary amine and at least one saturated or unsaturated hydrocarbon chain comprising at least nine carbon atoms. In a particular embodiment, the ionizable cationic lipid is dilinoleylmethyl-4-dimethylaminobutyrate (D-Lin-MC3-DMA; CAS 1224606-06-7).

In particular aspects of the above embodiments of the method, the assay diluent further includes a metal chelator, which in a further embodiment may be ethylenediaminetetraacetic acid (EDTA).

In particular aspects of the above embodiments of the method, the sample suspension is diluted at least two-fold with the assay diluent to provide the diluted sample solution. In a further embodiment, the sample suspension is diluted between two-fold and ten-fold with the assay diluent to provide the diluted sample solution.

In particular aspects of any one of the foregoing embodiments of the method, the RNA is at least 100 nucleotides in length. In a further embodiment, the RNA is 100 to 1000 nucleotides in length and in a further embodiment the RNA is more than 1000 nucleotides. In particular embodiments, the RNA is a messenger RNA (mRNA), which in particular embodiments encodes a polypeptide that is at least 30 amino acids in length. In a further embodiment, the mRNA includes a poly(A) tail at the 3' end of the mRNA and a cap structure at the 5' end of the mRNA.

In particular embodiments of any one of the foregoing embodiments, the diluted sample solution comprises between 4 and 40 μg/mL of the RNA. In particular embodiments, the diluted sample solution comprises RNA at a concentration such that the absorbance of the RNA at $\lambda_{max}$ is between 0.1 and 1 absorbance units.

In particular embodiments of any one of the foregoing embodiments, the surfactant and the alkylamine are each selected to be optically transparent at $\lambda_{max}$ wherein optically transparent is having a net absorbance in a one cm path length that is less than 0.1 absorbance units relative to air or water.

In particular embodiments of the method, the $\lambda_{max}$ is from about 250 to about 270 nm. In a further embodiment, the $\lambda_{max}$ is about 260 nm or about 266 nm.

In particular embodiments of any one of the foregoing embodiments, the $\lambda_{max}$ is measured using an apparatus capable of measuring UV absorbance of RNA, for example a UV/visible light spectrometer.

DETAILED DESCRIPTION OF THE INVENTION

Definitions

Figure 1A:
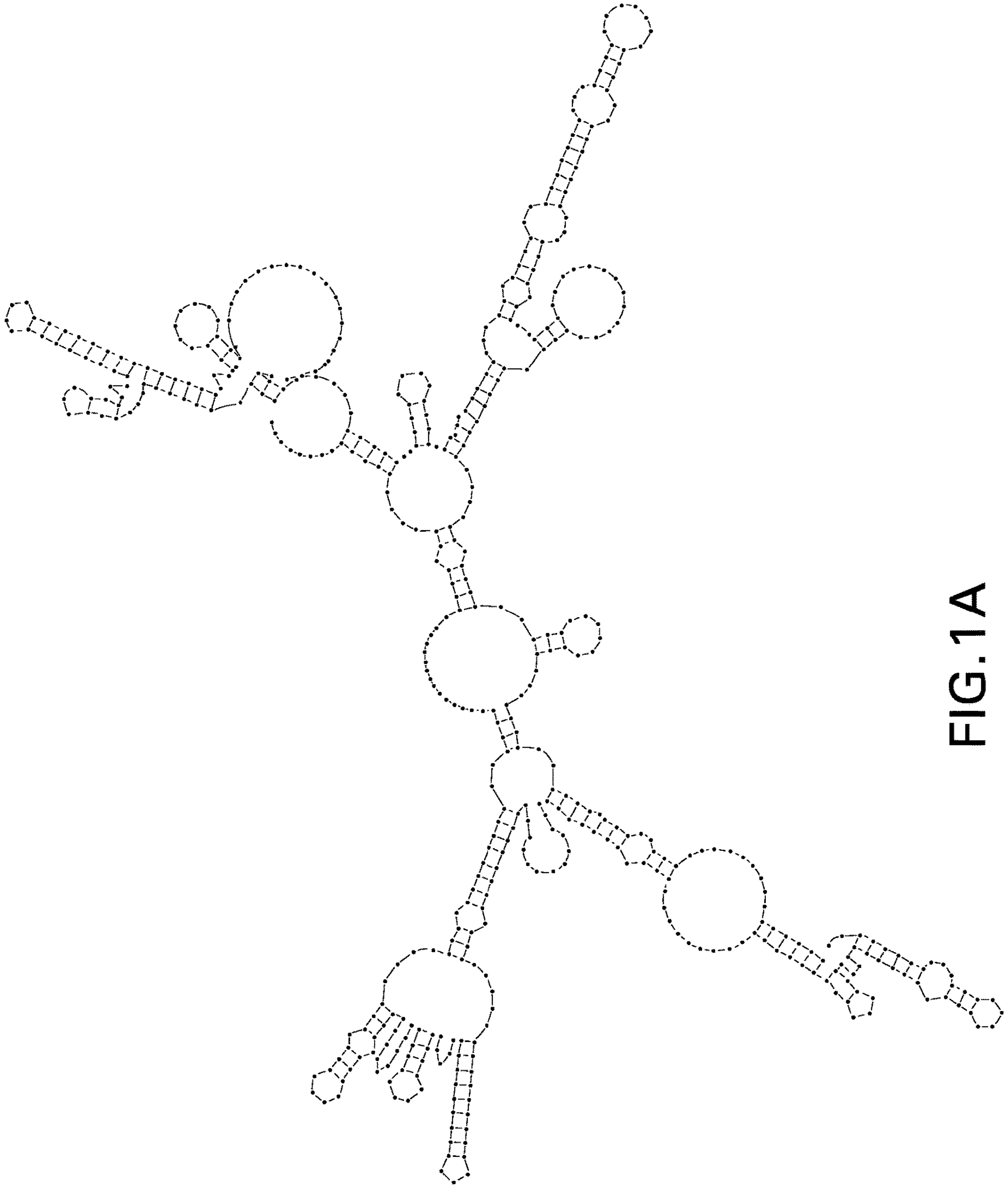
FIG. 1A: Illustrates the complex secondary structure that may be adopted by an mRNA molecule in an aqueous solution at physiological pH.

The term "alkyl" as used herein refers to saturated, straight- or branched-chain hydrocarbon radicals derived from a hydrocarbon moiety by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkylamine" as used herein refers to primary, secondary, or tertiary alkylamines. A primary alkylamine may be represented by the formula $NH_2R$ or $H_2N—R$ wherein R is an alkyl or aryl group; a secondary alkylamine may be represented by the formula NHRR' or

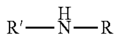

wherein R and R' are each independently an alkyl or aryl group; and, a tertiary alkylamine may be represented by the formula NRR'R" or

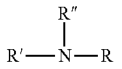

wherein R, R', and R" are each independently an alkyl or aryl group.

The term "amino lipid" as used herein refers to those lipids having one, two, or more fatty acid or fatty alkyl chains and an amino head group (including an alkylamino or dialkylamino group) that may be protonated to form a cationic lipid at or below physiological pH.

The term "cationic lipid" as used herein include any biodegradable cationic lipid suitable for forming a lipid nanoparticle. Preferably, the cationic lipid will have a net positive charge at about physiological pH. The cationic lipid may be an amino lipid. The amino or cationic lipids have at least one protonatable or deprotonatable group, such that the lipid is predominantly positively charged at a pH at or below physiological pH, and increasingly neutral as the pH is adjusted upward above the physiological pH.

The term "lipid nanoparticle" or "LNP" refers to a transfer vehicle comprising one or more lipids (e.g., cationic lipids, non-cationic lipids, and PEG-modified lipids), which has been formulated to deliver one or more mRNA to one or more target cells.

The term "messenger RNA" or "mRNA" refers to a nucleotide polymer comprising predominantly ribonucleotides and encoding a polypeptide or protein. mRNA typically comprises from 5' to 3', a 5' guanosine cap structure, a 5' untranslated (UT) region, an open reading frame (ORF) encoding a protein or polypeptide, a 3' UT region, and a 3' poly(A) tail comprising about 100 to 200 adenosine residues. The typical mRNA will comprise about 1,000 to 2,000 nucleotide residues. In particular embodiments, the mRNA molecule may comprise one or more modified or non-natural nucleotide residues.

The term "optically transparent" refers to having a net absorbance in a one cm path length that is less than 0.1 absorbance units relative to air or water.

The term "physiological pH" refers to having a pH of about 7.4 pH units.

The term "ribonucleic Acid" or "RNA" refers to a nucleotide polymer comprising predominantly ribonucleotides. As used herein, the term is intended to encompass any RNA molecule of at least 100 nucleotides in length, including messenger RNA. Typically, an RNA molecule will comprise a combination of nucleotide residues selected from adenosine (A), guanosine (G), uracil (U), and cytosine (C) residues. In particular embodiments, the RNA molecule may comprise one or more modified nucleotides, one or more non-natural nucleotide residues, or both one or more modified nucleotides and one or more non-natural nucleotide residues.

The term "surfactant" as used herein refers to an organic compound that is amphiphilic, having both hydrophobic groups and hydrophilic groups. The surfactant may be an ionic surfactant such as sodium dodecyl sulfate (SDS) or a non-ionic surfactant such as a polyethylene glycol alkyl ether.

Method for Measuring RNA Concentration

Figure 1B:
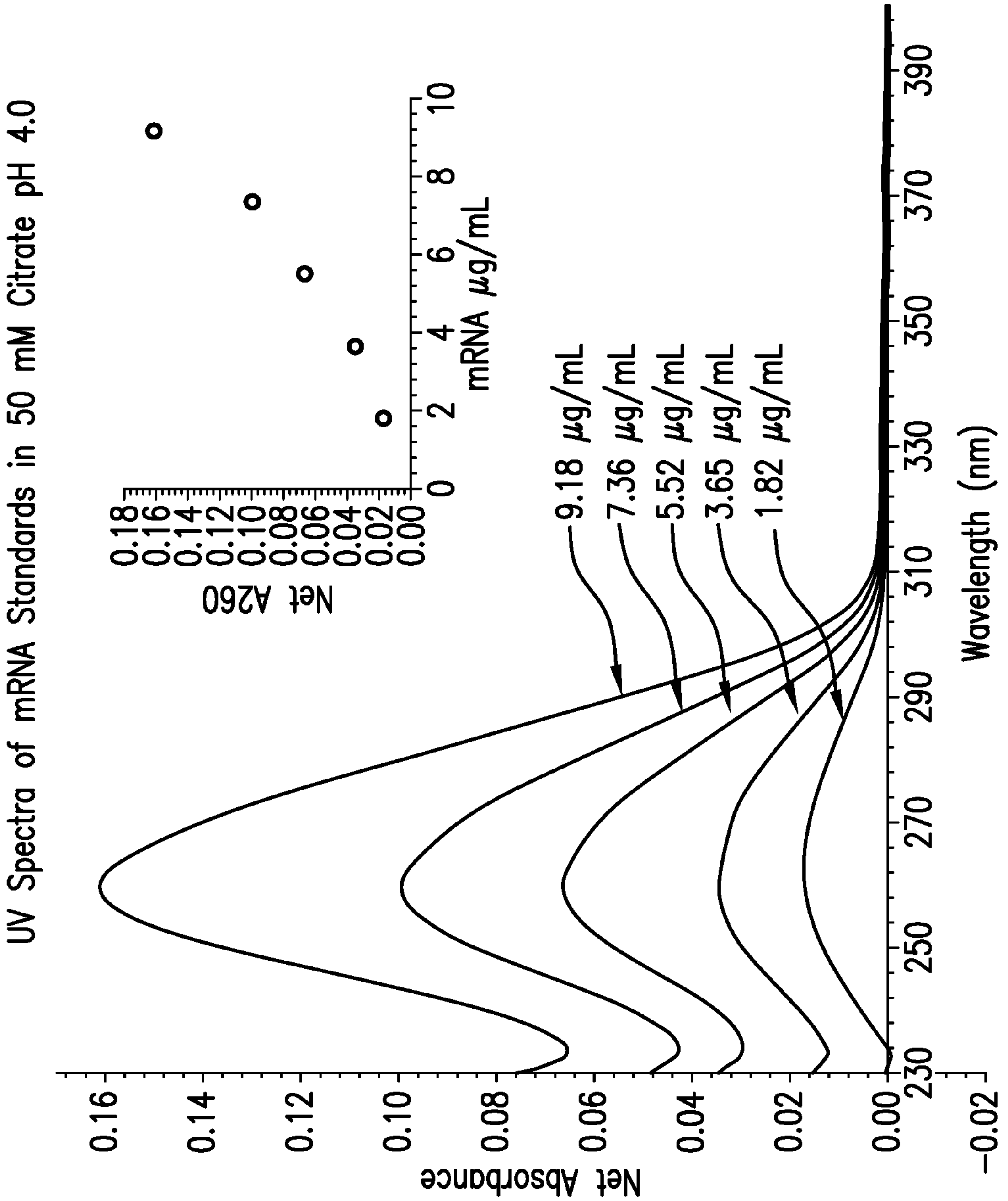
FIG. 1B: Graph showing the typical UV spectra for varying concentrations of mRNA standards in 50 mM citrate buffer at pH 4.0 at room temperature. Inset chart casts the Net Absorbance values at 260 nm against the concentrations, highlighting the non-linear relationship.
Figure 1C:
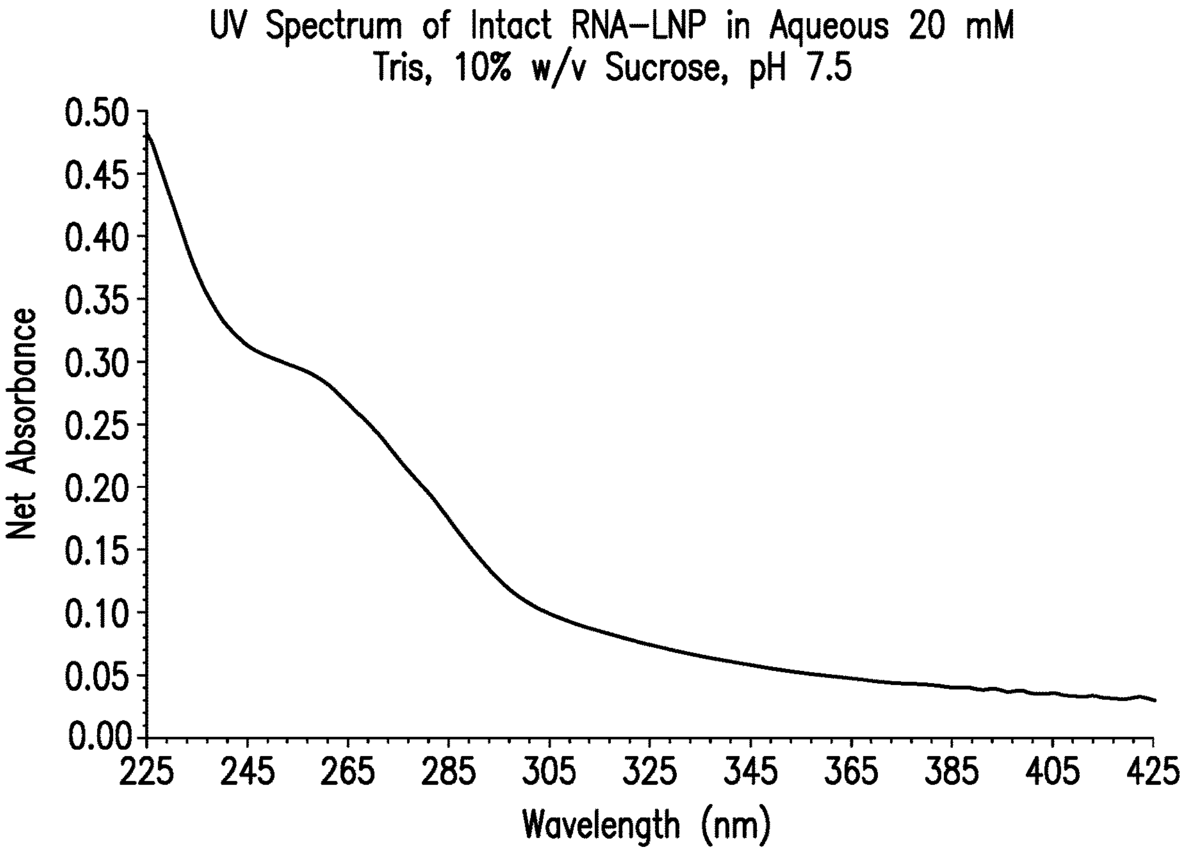
FIG. 1C: Graph showing the UV spectrum of a typical intact RNA-LNP at room temperature in a Tris/sucrose solution containing no co-solvents or surfactants. When the RNA-LNP is intact, a low broad absorbance band corresponding to RNA appears superimposed on a large exponentially-decaying background caused by scattering from the LNP.
Figure 1D:
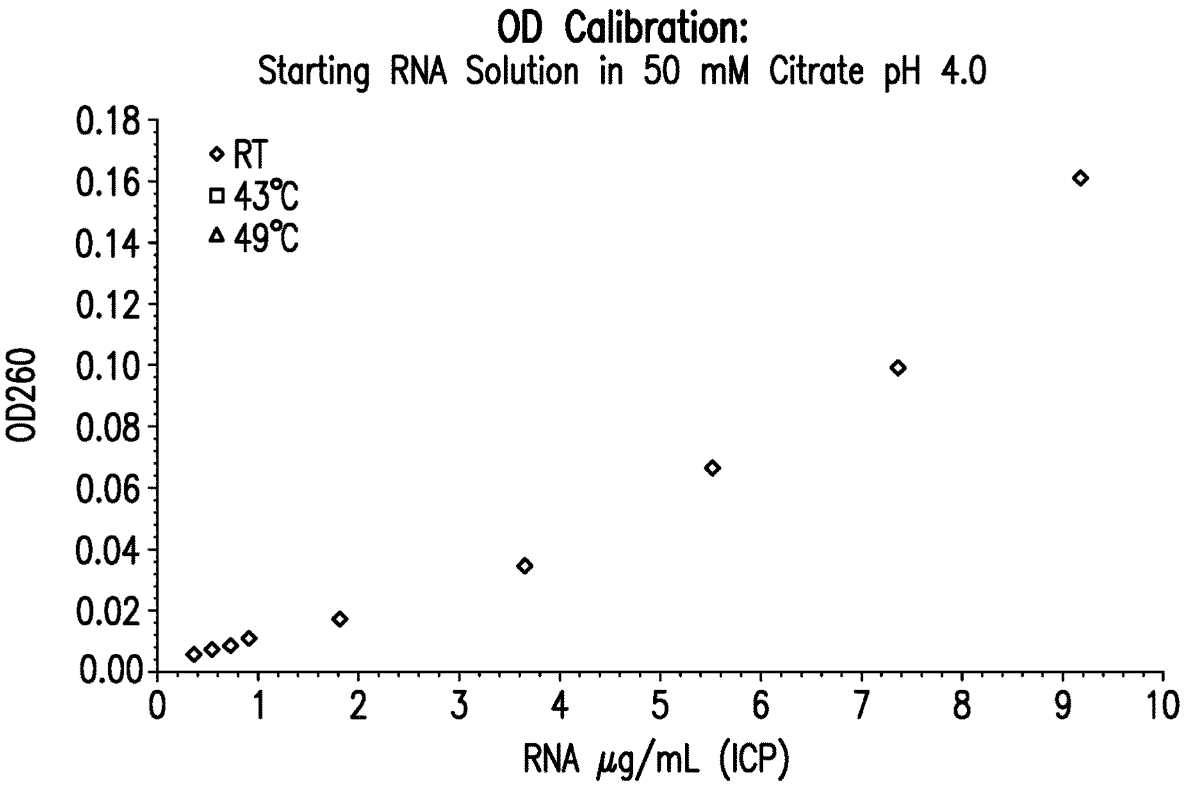
FIG. 1D: shows a graph plotting the absorbance at $A_{260}$ vs. RNA concentration at room temperature and the effect of temperature on $A_{260}$ at a particular concentration.
Figure 1E:
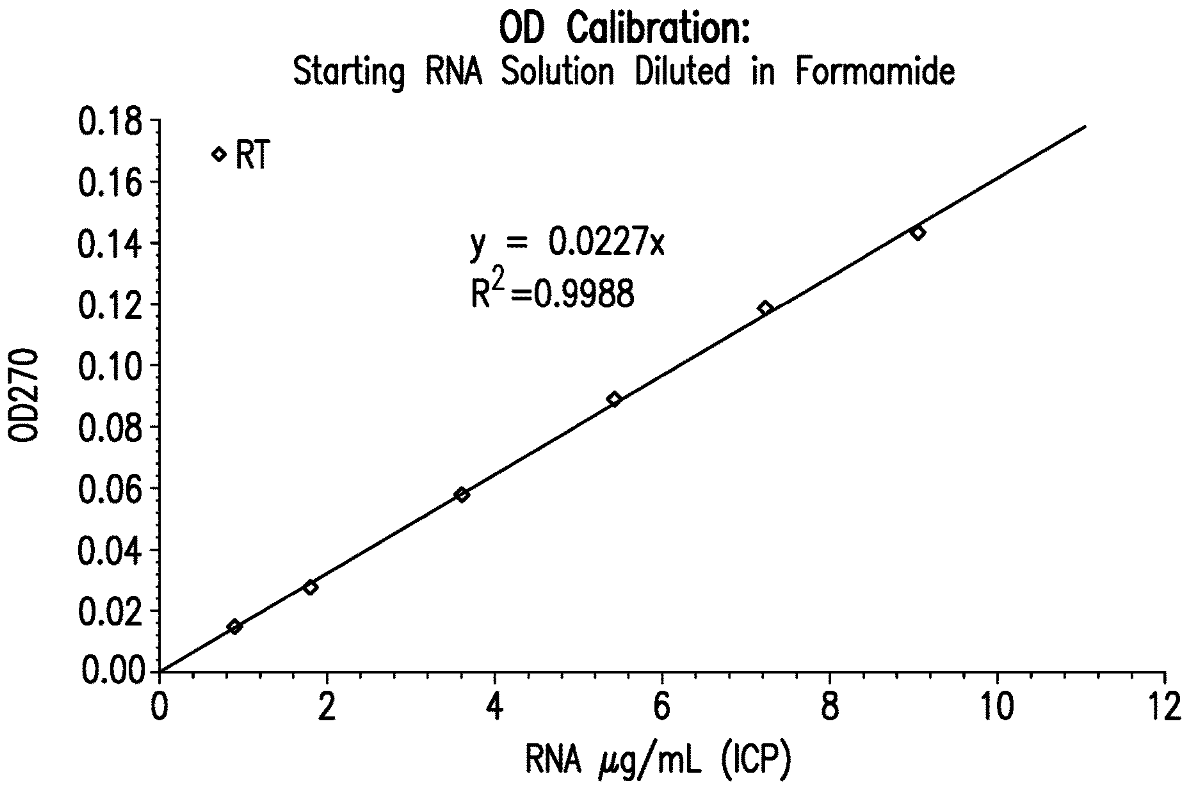
FIG. 1E: shows a graph plotting the absorbance at $A_{260}$ vs. RNA concentration at room temperature for RNA completely denatured in formamide and at room temperature.

The traditional method for measuring RNA concentration and purity is UV spectroscopy. The absorbance of a diluted RNA sample is measured at λmax of RNA, which is about 260 nm, and at 280 nm and the nucleic acid concentration is calculated using the Beer-Lambert law, which predicts a linear change in absorbance with concentration. However, accurate determination of mRNA content in solutions, particularly in the context of LNPs is experimentally complicated owing to the appearance of manifold secondary structures in solution arising from complementary sequence regions within the RNA that are capable of forming intramolecular and intermolecular base pairing (See FIG. 1A for a representative view of mRNA secondary structure). Temperature, pH, solvents, and other factors are all known to influence the formation of these complex and dynamic secondary structures. Because the optical extinction coefficients for single-versus double-stranded RNA segments are different and because the various folded states exhibit differential binding to ion-exchange media, the experimental determination of mRNA content by means of either UV spectrometry or ion-exchange chromatographic methods is non-trivial and often problematic. Data collected from these techniques frequently demonstrate non-linearity, poor reproducibility, and other technical problems. Compare the ideal UV spectra for differing concentrations of an mRNA denatured in an aqueous solution shown in FIG. 1B to the less than ideal UV spectrum of a typical intact LNP containing the mRNA shown in FIG. 1C. To accurately measure the concentration of RNA, the absorbance vs concentration of the RNA should be linear. As shown in FIG. 1D, the UV absorbance of non-denatured RNA in solution vs RNA concentration is non-linear when measured at the $\lambda_{max}$ for the RNA and as can be seen, the absorbance at the $\lambda_{max}$ for the RNA changes in response to changes in temperature. FIG. 1E shows that for RNA completely denatured with formamide, the absorbance of the denatured is linear to its concentration. However, formamide is not useful for measuring the concentration of denatured RNA because it absorbs at the $\lambda_{max}$ for the denatured RNA.

To accurately measure mRNA content in solutions comprising mRNA containing LNPs (RNA-LNPs) using UV absorbance, the following four conditions need to be met.

(1) The measuring conditions must completely disrupt the LNP containing the mRNA either by the action of a surfactant or a strong co-solvent.

(2) The measuring conditions must completely disrupt the LNP and denature the mRNA, typically by maintaining, for example, at least one of the following conditions: (i) increasing the temperature of an aqueous solution of the RNA-LNP to at least 70° C.; (ii) adding at least 50% v/v of formamide or DMSO to an aqueous solution of the RNA-LNP; or (iii) increasing the pH of the aqueous solution of the RNA-LNP to about 12 pH units.

(3) The mRNA should also be free of bound ionizable cationic lipids because the UV spectrum of a sample containing partially or even completely denatured LNP and mRNA is slightly altered by the presence of the strongly complexing ionizable cationic lipids comprising the LNP and which constitutes a majority of the LNP by weight.

(4) The UV absorbance method conditions must provide for sufficient optical transparency at $\lambda_{max}$ to allow for measurement of mRNA content, e.g., nominally transparency at about 260 nm.

The method of the present invention meets all four conditions. The method includes a surfactant that is capable of disrupting or dissociating the RNA-LNP in an aqueous solution into its RNA and other components such as its ionizable cationic lipids and an alkylamine, which (i) raises the pH of the aqueous solution to about pH 12 thereby denaturing the RNA and (ii) displaces ionizable cationic lipids bound to the RNA, to provide an aqueous solution of denatured RNA free of bound ionizable cationic lipids and optically transparent at the $\lambda_{max}$ of the RNA. The Examples exemplify an embodiment of the present invention in which the surfactant is SDS and the alkylamine is N,N-dimethylbutylamine (DMBA; CAS 927-62-8).

Thus, the present invention provides an absorbance method that can measure the RNA content of samples of RNA-LNPs. The method for measuring the RNA concentration of a suspension of RNA-lipid nanoparticle (RNA-LNPs) comprises (a) providing a sample suspension comprising RNA-LNPs wherein the RNA-LNPs comprise ionizable cationic lipids; (b) mixing the sample suspension of RNA-LNPs with an assay diluent comprising a surfactant and an alkylamine to provide a diluted sample solution in which the RNA is denatured and dissociated from or not bound to the ionizable cationic lipids; (c) obtaining (i) a Net Absorbance of the dilute sample solution by measuring absorbance at $\lambda_{max}$ of the RNA in the diluted sample solution comprising the dissociated denatured RNA and LNP components or (ii) obtaining an adjusted Net Absorbance by measuring absorbance of the diluted sample solution at $\lambda_{max}$ of the RNA in the diluted sample solution and absorbance of the diluted sample solution at 400 nm and subtracting the absorbance at 400 nm from the absorbance from $\lambda_{max}$ to provide an adjusted Net Absorbance; and (d) using the Net Absorbance or the adjusted Net Absorbance to provide the RNA concentration of the suspension of RNA-lipid nanoparticle (RNA-LNPs).

The RNA concentration may be determined using the formula $$mRNA\left(\frac{mg}{mL}\right)=\left(\frac{\text{Net Absorbance or adjusted Net Absorbance}}{\text{path length (cm)}}\right)\times\left(40\ \frac{\mu g\cdot cm}{mL}\right)\times\left(\frac{1\ \frac{mg}{mL}}{1000\ \frac{\mu g}{mL}}\right)\times\text{Dilution Factor}$$

wherein $$\text{Dilution Factor}=\frac{\text{Diluted Sample Solution volume }(\mu L)}{\text{Initial Sample Suspension volume }(\mu L)}$$

Net Absorbance is the absorbance at $\lambda_{max}$ and adjusted Net Absorbance is absorbance at $\lambda_{max}$–absorbance at 400 nm.

In general, the alkylamine selected is an alkylamine that when in the diluted sample solution results in a solution having a pH at about 11 pH units or more or about pH 12 or a pH of at least pH 12. The alkylamine is present in the diluted sample solution at a concentration sufficient to completely displace ionizable cationic lipids from the RNA. In particular embodiments of the method, the alkylamine comprises a tertiary amine of the formula NRR'R" wherein R, R', and R" are each independently a C1 to C18 alkyl. In a further embodiment, the alkylamine is selected from the group consisting of N,N-dimethylbutylamine (DMBA; CAS 927-62-8), N,N-diethylethanamine (TEA; CAS 121-44-8), N,N-diisopropylethylamine (DIPEA; CAS 7087-68-5), and hexan-1-amine (1-HA; CAS 111-26-2).

In general, the surfactant selected is capable of disrupting or dissociating RNA-LNP complexes into its RNA and lipid components. In particular embodiments, the surfactant is selected from the group consisting of sodium dodecyl sulfate (SDS; CAS 151-21-3), cetyltrimethylammonium bromide (C-TAB; CAS 57-09-0), and polyethylene glycol alkyl ether. In a particular embodiment, the surfactant is SDS and the alkylamine is DMBA or the surfactant is a polyethylene glycol alkyl ether and the alkylamine is 1-HA. In a further embodiment, the surfactant is polyethylene glycol hexadecyl ether (or polyoxyethylene (20) cetyl ether) CAS 9004-95-9 having the formula $HO—(CH_2CH_2O)_{20}—(CH_2)_{15}—CH_3$ and is marketed as BRIJ®-58.

In particular embodiments of the method, the assay diluent further includes a metal chelator, which in a further embodiment may be metal chelator is ethylenediaminetetraacetic acid (EDTA).

In particular embodiments of the method, the assay diluent comprises about 750 mM N,N-dimethylbutylamine, about 10% w/v SDS, and about 1 mM EDTA.

In particular embodiments of the method, the sample solution is diluted at least two-fold with the assay diluent to provide the diluted sample solution. In a further embodiment, the sample solution is diluted between two-fold and ten-fold with the assay diluent to provide the diluted sample solution.

In particular embodiments of the method, the diluted sample solution comprises between 4 and 40 μg/mL of the RNA. In particular embodiments, the sample solution comprises RNA at a concentration such that the absorbance of the RNA at $\lambda_{max}$ is between 0.1 and 1 absorbance units.

In particular embodiments of the method, the surfactant and the alkylamine are each selected to be optically transparent at $\lambda_{max}$ wherein optically transparent is having a net absorbance in a one cm path length that is less than 0.1 absorbance units relative to air or water.

In particular embodiments of the method, the diluted sample solution has a pH of at least 11 pH units or a pH of at least or about 12 pH units, which the inventors have discovered is sufficient in the presence of alkylamine (e.g., DBMA) and surfactant (e.g., SDS) to disrupt the RNA-LNPs into its components, denature the RNA of the disrupted LNP, and to displace cationic lipids that may be bound to the RNA.

In particular embodiments of the method, the $\lambda_{max}$ is from about 250 to about 270 nm. In a further embodiment, the $\lambda_{max}$ is about 260 nm or about 266 nm.

In particular embodiments of the method, the $\lambda_{max}$ is measured using an apparatus capable of measuring ultraviolet (UV) absorbance of RNA, for example a UV/visible light spectrometer.

Exemplary Lipid Nanoparticles

Exemplary RNA-LNPs that may be analyzed according to the present invention comprise a cationic lipid, a PEG-modified lipid, a sterol, and a non-cationic lipid. In some embodiments, the cationic lipid is an ionizable cationic lipid and the non-cationic lipid is a neutral lipid, and the sterol is a cholesterol. The cationic lipid may comprise a tertiary or secondary amine. In further embodiments, the RNA-LNP comprises a tertiary cationic lipid. In some embodiments, the cationic lipid is selected from the group consisting of 2,2-dilinoleyl-4-dimethylaminoethyl-[1,3]-dioxolane (DLin-KC2-DMA), dilinoleylmethyl-4-dimethylaminobutyrate (DLin-MC3-DMA), di((Z)-non-2-en-1-yl) 9-((4-(dimethylamino)butanoyl)oxy)heptadecanedioate, and (12Z, 15Z)-N,N-dimethyl-2-nonylhenicosa-12,15-dien-1-amine, and N,N-dimethyl-1-[(1S,2R)-2-octylcyclopropyl]heptadecan-8-amine. In particular embodiments, the RNA-LNP may comprise the ionizable cationic lipid dilinoleylmethyl-4-dimethylaminobutyrate (D-Lin-MC3-DMA; CAS 1224606-06-7), which has the structure

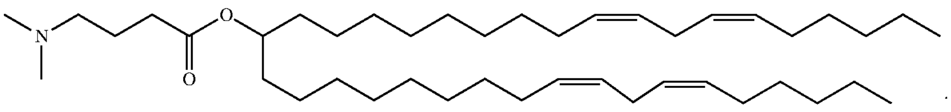

In particular embodiments, the RNA-LNP may comprise at least one of the ionizable cationic lipids selected from the group consisting of

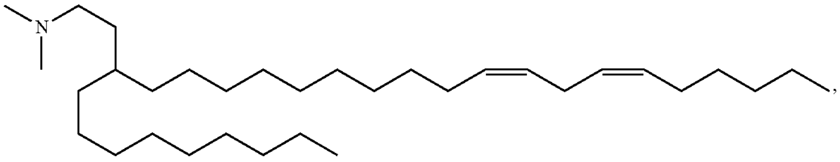,

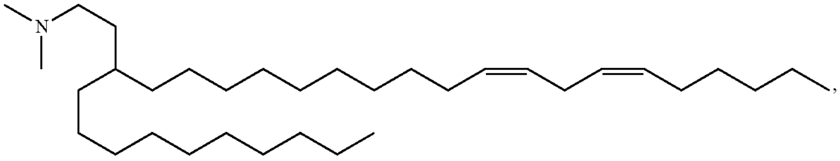,

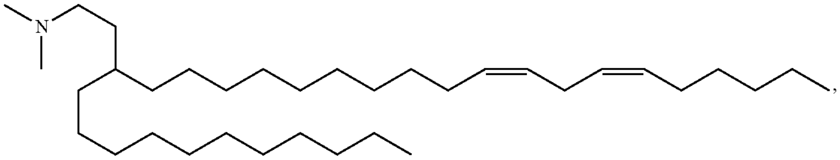,

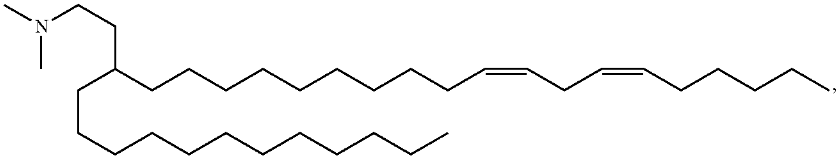,

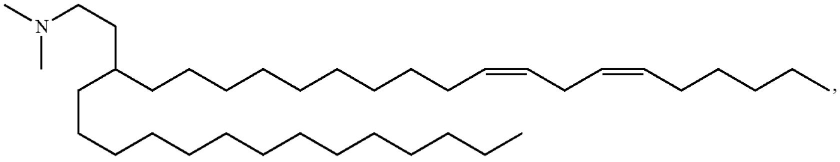,

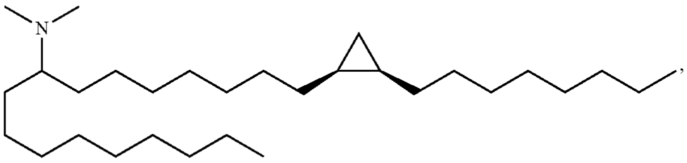,

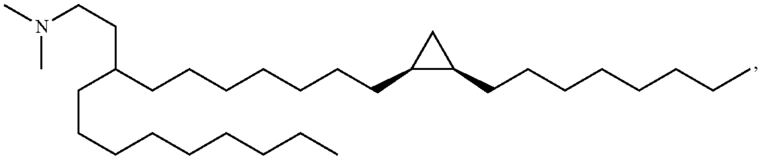,

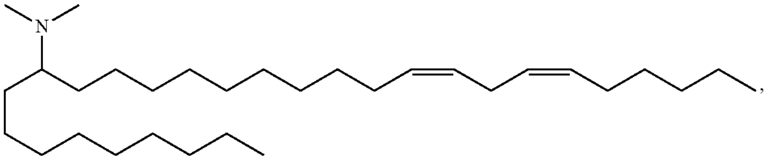,

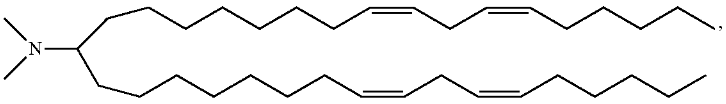, and

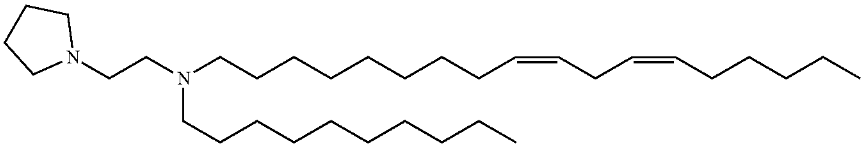

In particular embodiments, the RNA-LNP may comprise any ionizable cationic lipid suitable for use in preparing RNA-LNPs, for example, the ionizable cationic lipid series disclosed by Sabnis et al. in Molec. Thera. 26: 1509-1519 (2018) and Jayaraman et al. in Angew. Chem. Int. Ed. 51: 8529-8533 (2012). In particular embodiments, the cationic lipids may be selected from any of the cationic lipids disclosed in published International Patent Applications WO2017070622 and WO2018170260, each of which is incorporated herein by reference.

Exemplary Embodiment

In an exemplary embodiment of the present invention, aqueous solutions of mRNA standards and test samples are provided and mixed with aliquots of a concentrated SDS solution, a DMBA solution, and an EDTA solution to provide an mRNA solution comprising about 10% w/v SDS, about 750 mM DMBA, and about 1 mM EDTA. The resulting aqueous solution, which has a pH of about 11-12 pH units, completely disrupts the mRNA containing LNPs and mRNA secondary structure at ambient temperature, and the SDS and DMBA are sufficiently transparent to allow for direct determination of mRNA content by measuring optical density of the aqueous solution at 266 nm (this value representing the red-shifted $\lambda_{max}$ of the mRNA complexed with DMBA and/or the cationic lipid). Moreover, the SDS and DBMA are inexpensive and readily available in pure form. Specifically, the SDS disrupts the LNP structures in the sample and the excess DMBA in the SDS solution helps denature the mRNA and displace LNP ionizable cationic lipids bound to the mRNA.

Figure 5:
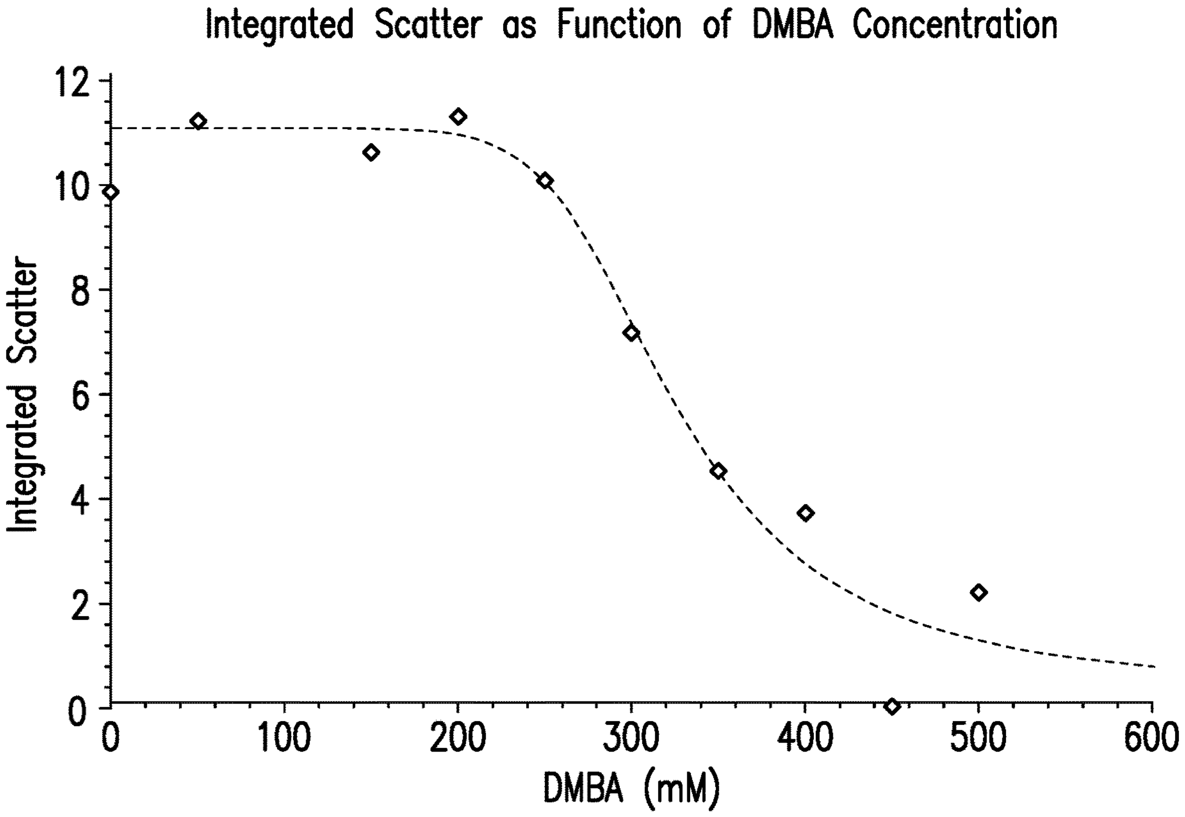
FIG. 5: Graph showing the displacement of cationic lipid MC3 from the mRNA molecule by DMBA as measured by the decrease in light scattering as a function of DMBA concentration.
Figure 6:
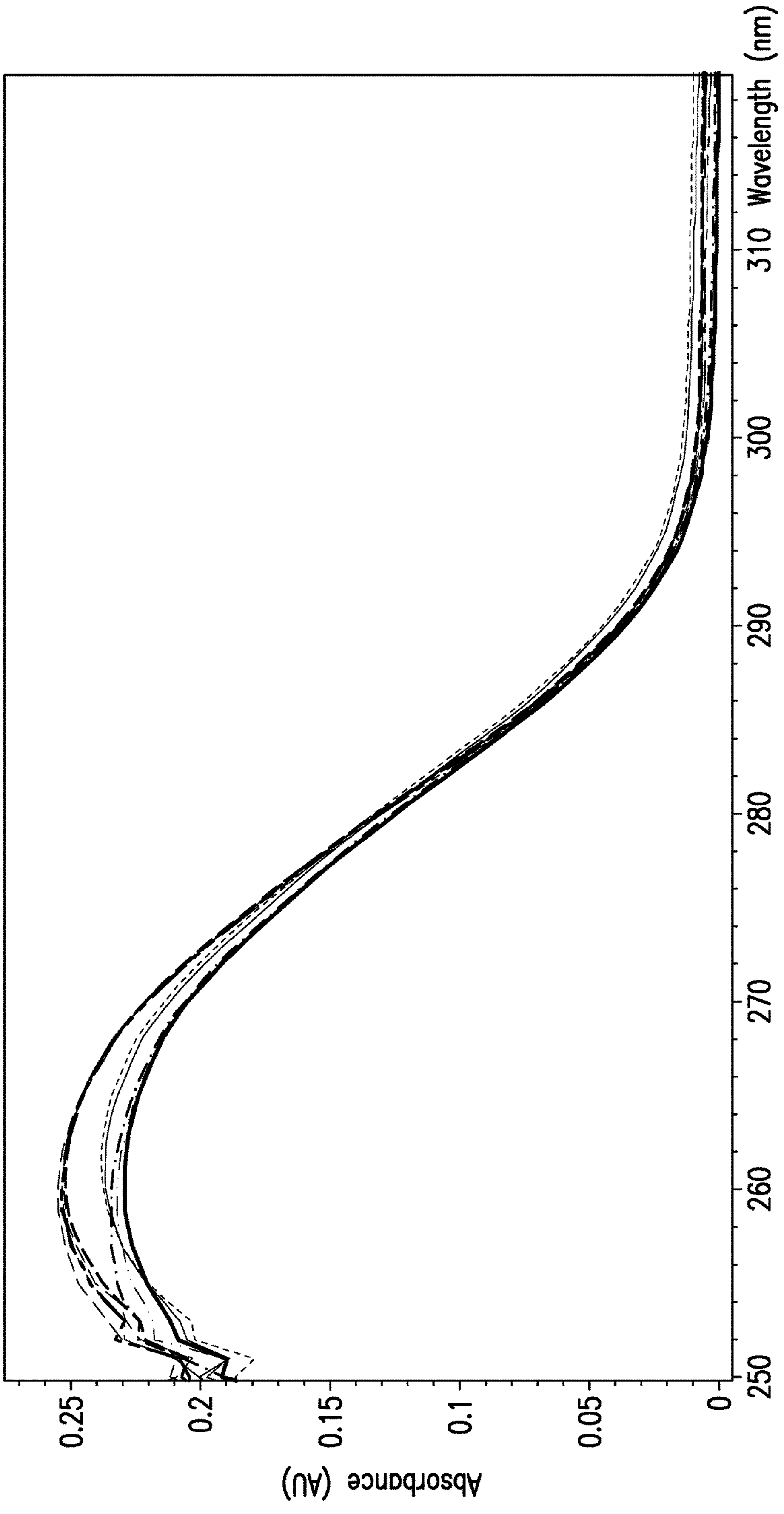
FIG. 6: Overlaid UV Spectra for multiple mRNA Standards and mRNA LNP samples prepared in 10% w/v SDS, 750 mM DMBA.

As shown in FIG. 6, addition of a large excess of DMBA to SDS solutions comprising mRNA standards or mRNA obtained from RNA-LNPs by the method of the present invention nearly collapses the spectra of the mRNA standard and mRNA in the LNP sample to the same $\lambda_{max}$. Also, as shown in FIG. 5, there is no scattering observed at 750 mM DBMA, which means the DMBA has displaced the cationic lipids bound ionically to the mRNA thereby rendering the mRNA free of bound lipids. The EDTA in solution helps to improve the stability of sample for up to about nine hours (see FIG. 7).

The following examples are intended to promote a further understanding of the present invention.

EXAMPLE 1

RNA secondary structure may be disrupted using heat, high pH, or an organic solvent such as formamide or DMSO.

Figure 2:
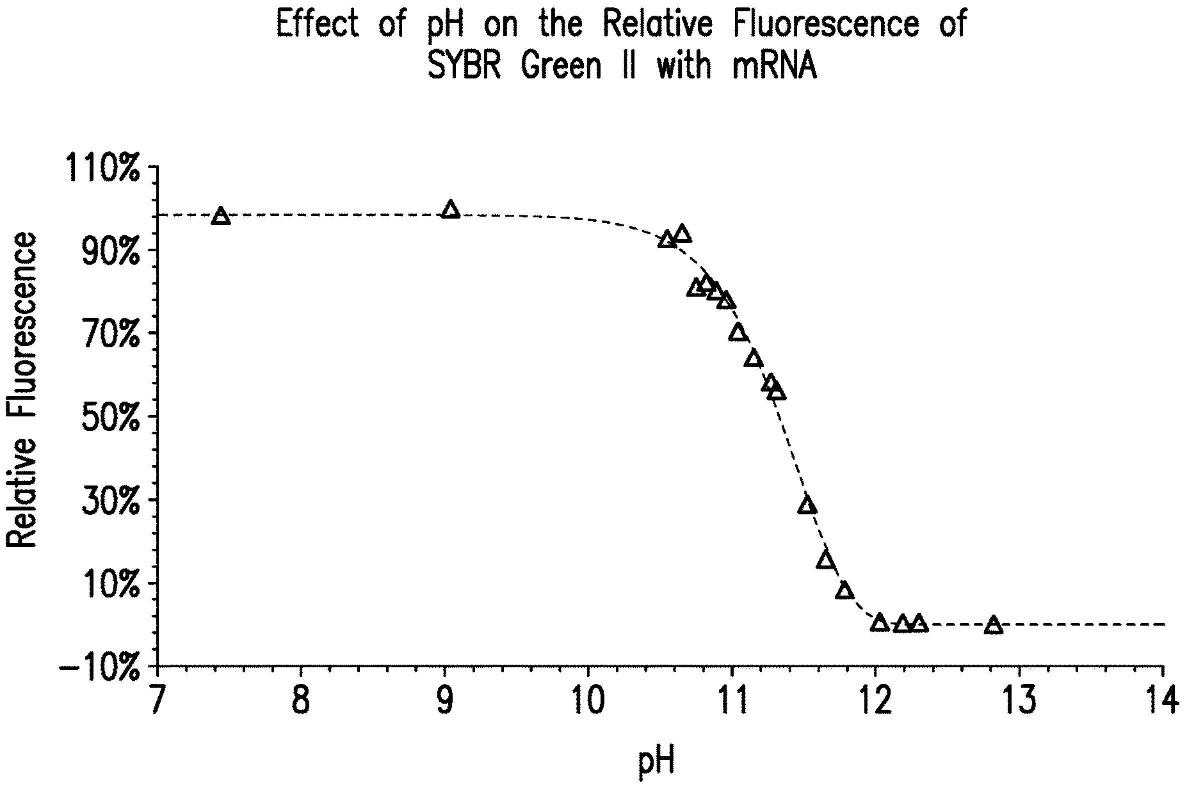
FIG. 2: Graph showing the denaturation of mRNA as a function of pH only. Aqueous solutions containing constant amounts of mRNA and SYBR Green II were prepared having pH values ranging from 7.5 to 13 and the relative fluorescence values were measured.

Representative mRNA comprising the mRNA having the components set forth in Table 1 or variant thereof was incubated in a series of aqueous solutions comprising SYBR Green II over a pH range beginning at pH 7.5 and ending at about pH 13. The relative fluorescence of each of the solutions was measured using a fluorimeter. SYBR Green II is a dye that fluoresces only when intercalated between double-stranded nucleotide base pairs. As shown in FIG. 2, incubating the mRNA at pH 12 completely disrupts the secondary structure of the mRNA as there is no measurable fluorescence at pH 12 or higher indicating there is no secondary structure to intercalate the SYBR Green II. The results indicate that incubating mRNA at pH 12 will completely denature the mRNA with no detectable secondary structure. While the mRNA is completely denatured at pH 12, the mRNA is unstable at pH 12 and has a relatively short half-life; however, as shown in Example 2, adding EDTA can extend the stability of the RNA for up to nine hours.

Figure 3:
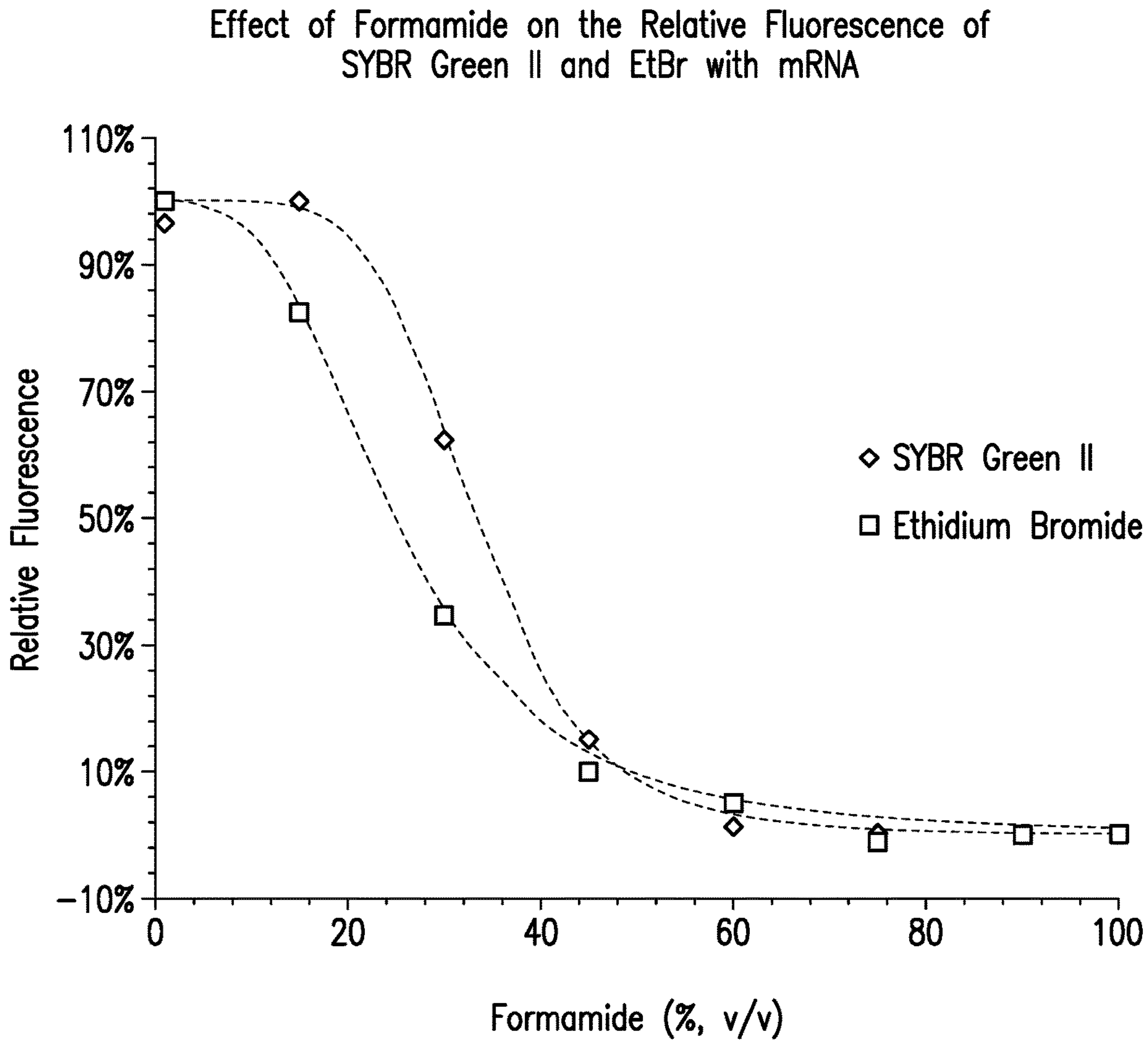
FIG. 3: Graph showing the denaturation of mRNA as a function of formamide content. Water-formamide solutions containing constant amounts of mRNA and either SYBR Green II or Ethidium Bromide were prepared having volume fractions of formamide ranging from 0% to 100% and the relative fluorescence values were measured.

Similarly, incubating the mRNA in increasing concentrations of formamide will completely denature the mRNA. For example, mRNA may be incubated in solutions comprising different concentrations of formamide and either SYBR Green II or ethidium bromide (another molecule that fluoresces when intercalated between base pairs of double-stranded regions in mRNA) and fluorescence measured by a fluorimeter. As shown in FIG. 3, mRNA incubated at room temperature in a solution containing formamide and SYBR Green II or ethidium bromide was completely disrupted when the formamide concentration was about 50% v/v. However, formamide is impractical for measuring mRNA content by UV absorbance of its absorbance over the range of wavelengths required to measure RNA concentrations by UV.

Figure 4:
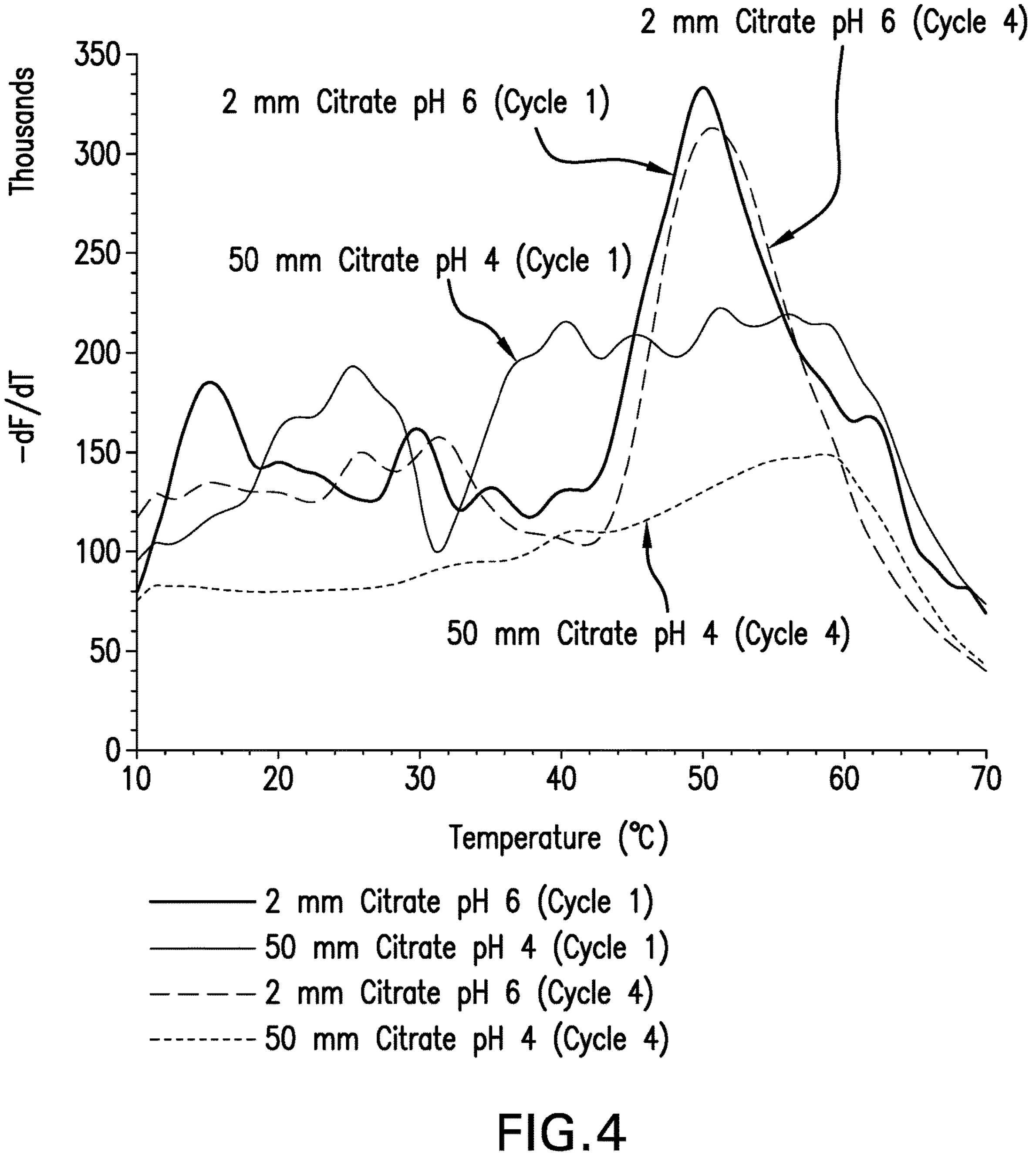
FIG. 4: Graph showing the denaturation of mRNA as a function of temperature. Aqueous solutions containing constant amounts of mRNA and SYBR Green II were subjected to multiple thermal gradients while measuring relative fluorescence. The first derivative of the relative fluorescence with respect to temperature (dF/dT) was plotted against temperature, yielding the complex curves shown here. It is clear from the graph that mRNA undergoes a complex series of unfolding events with increasing temperature, the folded states are not entirely reversible, and that a temperature of at least 70° C. must be maintained to keep the mRNA in a fully denatured state.

Fluorimetry was used to determine the minimum temperature required to maintain mRNA in a completely denatured state by purely thermal means. As shown in FIG. 4, the mRNA solution must be held at a minimum of 70° C. to maintain the mRNA in a fully denatured state. This is not practical for measuring mRNA content by UV absorbance.

EXAMPLE 2

The amount of DBMA acting in concert with SDS to achieve complete disruption of RNA-LNP complexes comprising ionizable cationic lipid MC3 and mRNA secondary structure, and to replace any MC3 complexed with the mRNA was determined as follows.

Aqueous solutions of RNA-LNPs comprising an mRNA having the components set forth in Table 1 or variant thereof were first diluted in 20% w/v SDS. Quickly and in succession, a constant amount of NaOH was added and increasing amounts of DMBA were then added to give final concentrations of 10% w/v SDS, 25 mM NaOH, and DMBA ranging from 0 mM to 500 mM. UV spectra were then collected for the mixtures and analyzed for residual light scattering by integrating the absorbance data from 320 nm to 800 nm. As shown in FIG. 5, the amount of light scattering decreased as the concentration of DMBA was increased (data represented by the solid diamonds). For the purposes of estimating the minimum amount of DMBA required under these conditions, a 5-parameter curve was fit through the data (result shown by the dashed line). Based upon the results, the concentration of DMBA required to achieve complete disruption of the mRNA secondary structure complex and displacement of the ionizable cationic lipid MC3 from the mRNA was determined to be at least 600 mM, more preferably, about 750 mM.

In a further experiment, aqueous solutions of mRNA standards and test samples were provided and mixed with aliquots of a concentrated SDS solution, DMBA solution, and an EDTA solution to provide an mRNA solution comprising about 10% w/v SDS, about 750 mM DMBA, and about 1 mM EDTA. The DBMA at 750 mM will raise the pH of the solution to about pH 12. The resulting aqueous solution completely disrupts the LNPs, completely eliminates mRNA secondary structure without heating, displaces ionizable cationic lipids from the mRNA, and remains sufficiently optically transparent to allow for direct determination of mRNA content at 266 nm (this value representing the red-shifted $\lambda_{max}$ of the mRNA complexed with DMBA and/or the cationic lipid). Moreover, the constituents are inexpensive and readily available in pure form. Specifically, the SDS and DMBA work in concert to completely disrupt the LNPs, competitively displace LNP cationic lipids bound to the mRNA, and simultaneously raise the pH to a level which completely denatures the mRNA.

In a further experiment, the role of DMBA in the method of the present invention was further probed by comparing the UV spectra obtained from final working-level preparations of both RNA-LNPs and an mRNA-only standard solutions in 10% w/v SDS containing 750 mM DMBA and 1 mM EDTA. As shown in FIG. 6, spectra for final working-level preparations of RNA-LNPs under these conditions exhibit spectra with a clear absorbance band at about 260 nm corresponding to mRNA and having no residual scatter as evident by the complete lack of absorbance above about 300 nm. This confirms that disruption of self-associated lipids is complete and no intact LNPs remain. However, close inspection of the spectra for both RNA-LNPs and mRNA-only standards shows that the observed $\lambda_{max}$ in the RNA-LNP spectra is slightly red-shifted from that of the mRNA-only standard. Whereas only the RNA-LNPs contain lipids, the slight difference could be attributable to some remaining association of one or more LNP lipids with mRNA in solution. Nevertheless, the conditions are clearly sufficient to provide for complete LNP disruption and mRNA denaturation as noted above and the remaining differences appear so slight as to not impart a meaningful difference in the method of the present invention.

Figure 7:
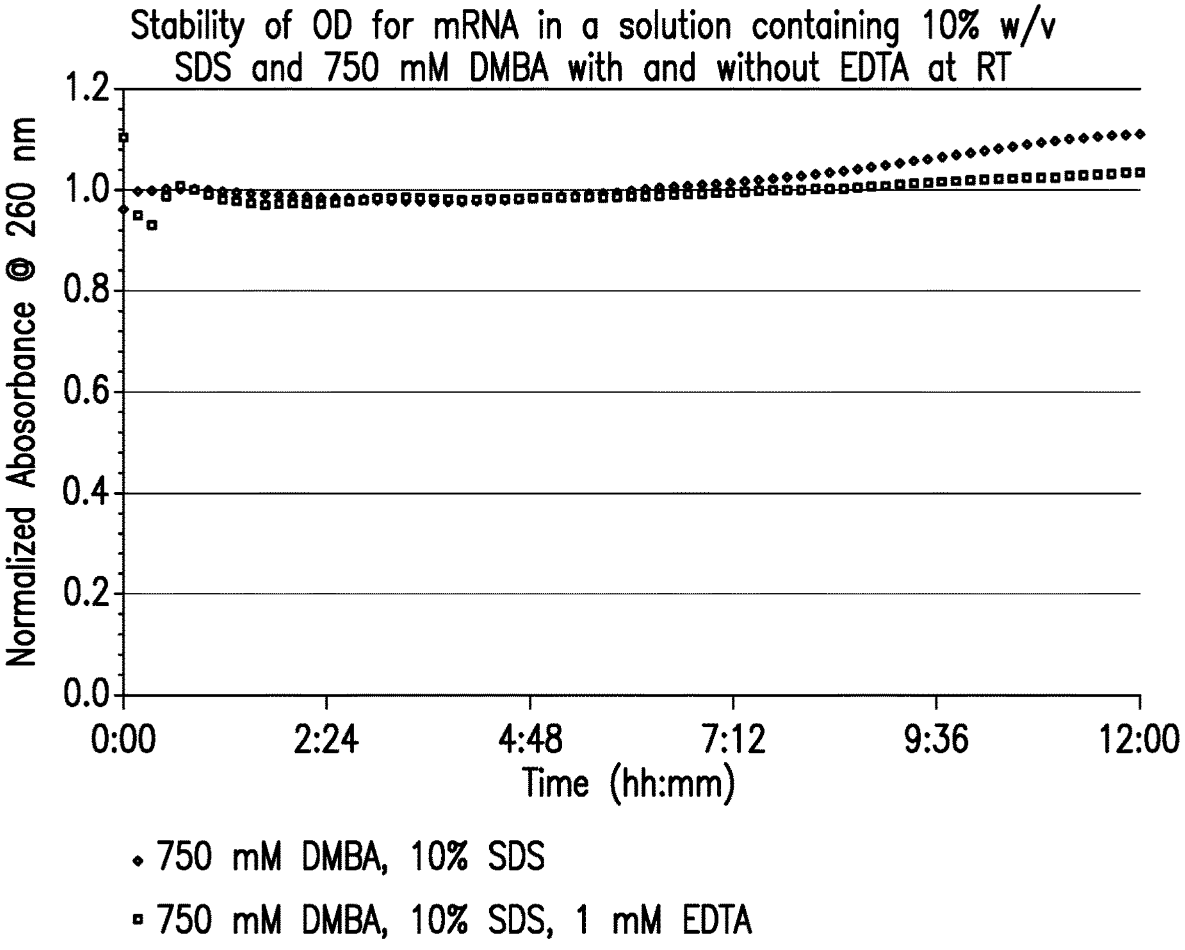
FIG. 7: Comparison of stability over time of optical density (OD) at $A_{260}$ for mRNA in 10% w/v SDS and 750 mM DMBA at room temperature with and without EDTA.

In a further experiment, the role of EDTA in the method of the present invention was further probed by collecting timed UV absorbance data at room temperature for final working-level preparations of an mRNA-only standard solution in 10% w/v SDS containing 750 mM DMBA both with and without 1 mM EDTA added. As shown in FIG. 7, absorbance measurements for both preparations are initially equivalent and stable. However, after about five hours, absorbance data for the preparation lacking EDTA begins to rise steadily whereas the absorbance data for the preparation comprising EDTA remains closer to initial OD. Thus, the data shows that EDTA in solution helps to improve the stability of sample for up to about eight hours at room temperature, which is adequate for practical analytical work (see FIG. 7).

EXAMPLE 3

The amount of formamide required to achieve complete denaturation of mRNA secondary structure was determined as follows.

Aqueous solutions were prepared containing constant amounts of an mRNA having the components set forth in Table 1 or variant thereof and either SYBR Green II or Ethidium Bromide but with increasing volume fractions of formamide. Fluorescence of either SYBR Green II or Ethidium Bromide was then measured for each solution using a spectrofluorimeter. Relative fluorescence values for either SYBR Green II or Ethidium Bromide were then compared to the values for each solution prepared in 100% v/v formamide. Both SYBR Green II and Ethidium Bromide act as probes of RNA denaturation because they exhibit very little fluorescence in aqueous solution but yield greatly enhanced fluorescence in the presence of folded RNA states owing to the propensity of these molecules to intercalate, fitting between stacked base pairs. As shown in FIG. 3, the relative fluorescence of both probes is maximal in the presence of the mRNA when the RNA is prepared in aqueous solutions having very little or no formamide. As the volume fraction of formamide increases, the mRNA is progressively denatured, which diminishes the population of stacked base pairs and thereby leads to a loss of fluorescence for the intercalating probes. Above about 60% v/v formamide, the relative fluorescence is effectively zero indicating complete denaturation of the mRNA.

EXAMPLE 4

Figure 8:
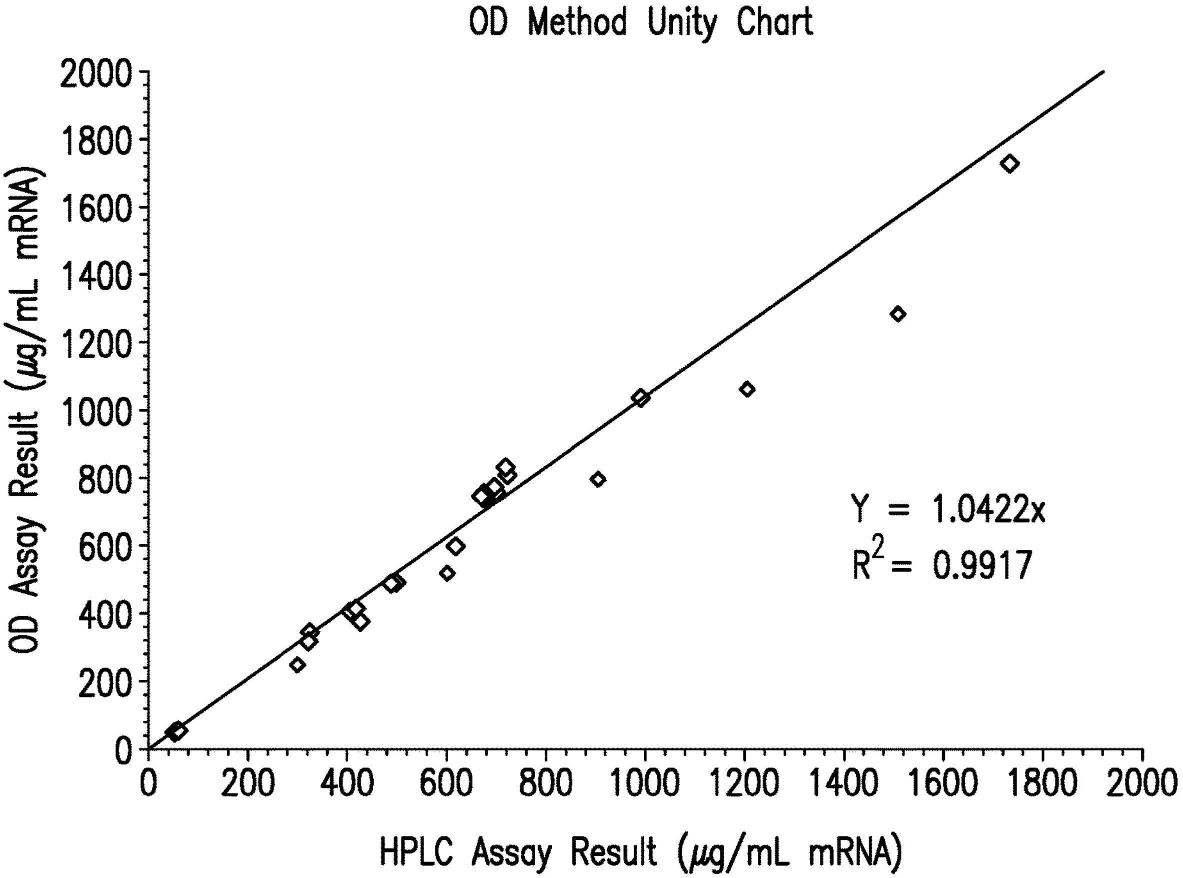
FIG. 8: Unity chart for assay results for a set of RNA-LNP test articles by the method of the present invention as compared to assay results obtained with a standard HPLC weak anion exchange (WAX) assay for a set of the same RNA-LNP test articles. Linear regression of the data yields a slope very close to 1 and a correlation coefficient close to 1, indicating good agreement between the two methods.

FIG. 8: Unity chart for assay results for a set of RNA-LNP test articles by the method of the present invention as compared to assay results obtained with a standard HPLC weak anion exchange (WAX) assay for a set of the same RNA-LNP test articles. Linear regression of the data yields a slope very close to 1 and a correlation coefficient close to 1, indicating good agreement between the two methods.

Figure 9:
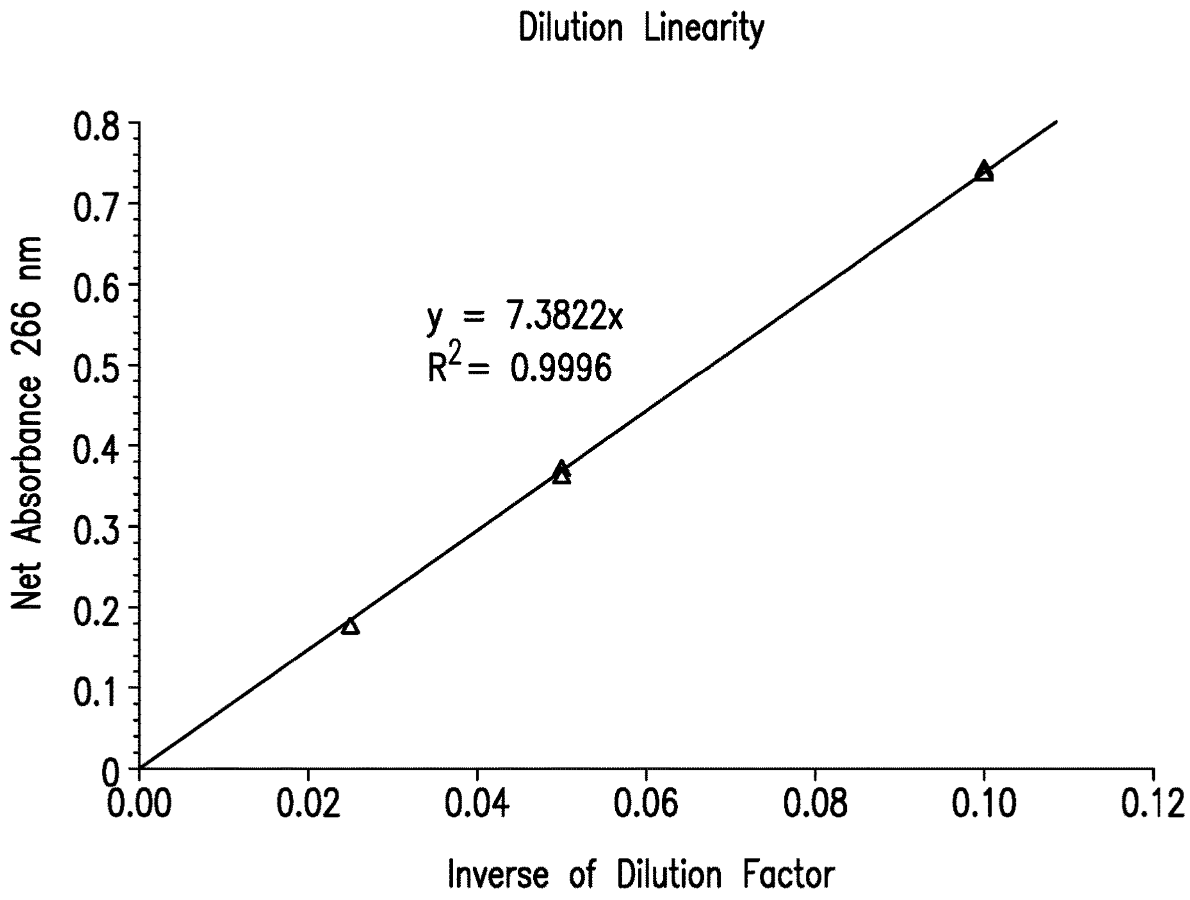
FIG. 9: Graph of Net Absorbance by the method of the present invention as a function of the inverse Dilution Factor for a given RNA-LNP test article. Linear regression with these data yields a correlation coefficient very close to 1, indicating excellent method linearity and providing the basis for a range of applicable working Dilution Factors which may be employed for actual RNA-LNP test articles.

FIG. 9: Graph of Net Absorbance by the method of the present invention as a function of the inverse Dilution Factor for a given RNA-LNP test article. Linear regression with these data yields a correlation coefficient very close to 1, indicating excellent method linearity and providing the basis for a range of applicable working Dilution Factors which may be employed for actual RNA-LNP test articles.

TABLE 1

| SEQ ID NO: | Description | Sequence |
|---|---|---|
| | 5′ Cap | m7G(5')ppp(5')G-2'-O-methyl |
| 1 | mRNA | GGGAAAUAAGAGAGAAAAGAAGAGUAAGAAGAAAUAUAAGAG<br>CCACCAUGGAACUGCUCAUUUUGAAGGCAAACGCUAUCACGAC<br>AAUACUCACUGCAGUGACCUUCUGUUUUGCCUCAGGCCAGAAC<br>AUAACCGAGGAGUUUUAUCAAUCUACAUGCAGCGCUGUAUCU<br>AAAGGCUACCUGAGUGCGCUCCGCACAGGAUGGUACACCUCCG<br>UGAUCACCAUCGAGCUCAGCAAUAUUAAAGAGAACAAGUGCA<br>AUGGUACCGACGCUAAAGUCAAACUUAUCAAGCAGGAACUCGA<br>CAAAUAUAAGAACGCUGUGACCGAGCUGCAGUUAUUGAUGCA<br>GAGUACACCUGCCACCAAUAACAGAGCUAGGAGGGAGUUGCCU<br>AGGUUUAUGAACUACACUCUCAACAACGCGAAGAAAACCAAUG<br>UGACGCUAUCCAAGAAACGGAAGAGGAGGUUCCUGGGGUUUC<br>UUUUAGGGGUGGGCUCUGCCAUUGCUUCCGGCGUGGCUGUAU<br>GUAAAGUUCUCCACCUCGAGGGAGAGGUUAAUAAGAUUAAGU<br>CGGCCCUGCUGAGUACUAACAAAGCAGUGGUGUCGCUGAGUAA<br>CGGAGUAAGUGUGUUAACAUUUAAGGUGCUGGACCUCAAGAA<br>UUAUAUUGACAAACAGUUGCUUCCUAUUCUAAACAAACAGAG<br>CUGUUCAAUAAGUAAUAUUGAAACUGUUAUUGAGUUUCAGCA<br>GAAGAACAACAGGCUUCUUGAGAUUACACGCGAGUUCAGUGU<br>CAAUGCCGGCGUUACAACACCCGUGUCUACCUACAUGCUGACG<br>AAUUCUGAGCUUCUCUCUCUCAUAAACGACAUGCCCAUUACGA<br>AUGACCAAAAGAAACUUAUGUCCAACAACGUGCAGAUUGUGC<br>GACAGCAAUCCUAUAGCAUUAUGUGUAUCAUCAAGGAAGAGG<br>UACUCGCUUAUGUUGUGCAGCUACCACUCUAUGGUGUGAUUG<br>ACACCCCCUGUUGGAAGCUGCAUACCAGUCCACUCUGCACCAC<br>UAACACAAAGGAAGGGAGCAAUAUUUGCCUCACUCGAACCGAC<br>AGGGGGUGGUAUUGCGAUAAUGCGGGCUCCGUGUCCUUCUUU |

TABLE 1-continued

| SEQ ID NO: | Description | Sequence |
|---|---|---|
| | | CCACAGGCUGAAACUUGUAAGGUACAGUCAAACCGCGUGUUCU<br>GUGAUACUAUGAAUUCUCUGACUCUUCCCAGCGAGGUUAAUCU<br>CUGCAACGUCGACAUUUUCAAUCCUAAAUAUGACUGCAAGAUC<br>AUGACCAGCAAGACCGACGUCUCCAGCUCAGUAAUCACUAGCC<br>UAGGGGCCAUUGUAAGCUGCUAUGGCAAAACCAAGUGUACUG<br>CCUCUAAUAAGAACAGAGGCAUAAUUAAAACCUUUUCAAAUG<br>GCUGUGACUAUGUGUCGAAUAAGGGCGUCGACACGGUCUCAG<br>UAGGGAAUACCCUCUACUACGUUAACAAACAGGAAGGCAAAUC<br>CCUUUAUGUAAAGGGCGAGCCCAUCAUAAAUUUCUACGACCCA<br>CUUGUGUUCCCCAGUGAUGAAUUCGAUGCAUCAAUCUCCCAGG<br>UGAACGAAAAGAUCAAUCAAUCCCUUGCUUUUAUACGAAAGU<br>CAGAUGAACUCCUGCAUAACGUGAAUGCUGGGAAAUCUACAAC<br>CAACAUCAUGAUCACUACCAUCAUUAUUGUGAUUAUCGUAAU<br>UCUGCUAUCCUUGAUUGCUGUCGGGCUGCUUCUGUACUGUAAG<br>GCCAGAUCGACGCCUGUGACCCUUUCAAAAGACCAACUUAGCG<br>GUAUCAAUAAUAUUGCCUUUAGCAAUUGAUAAUAGGCUGGAG<br>CCUCGGUGGCCAUGCUUCUUGCCCCUUGGGCCUCCCCCCAGCC<br>CCUCCUCCCCUUCCUGCACCCGUACCCCCGUGGUCUUUGAAUA<br>AAGUCUGAGUGGGCGGC |
| | Poly(A) Tail | 100 ribonucleotides |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for measuring the ribonucleic acid (RNA) concentration of a suspension of RNA-lipid nanoparticle (RNA-LNPs) wherein the RNA-LNPs comprise ionizable cationic lipids and the RNA is at least 100 nucleotides in length, the method comprising:

(a) mixing a suspension of RNA-LNPs comprising ionizable cationic lipids and RNA at least 100 nucleotides in length with an assay diluent comprising (i) a surfactant that disrupts the RNA-LNPs into their RNA and LNP components and is optically transparent at $\lambda_{max}$ of the RNA and (ii) an alkylamine that denatures the RNA by providing a pH of at least pH 11 or about pH 12, displaces the ionizable cationic lipids of the LNP that are associated with or complexed to the denatured RNA, and is optically transparent at $\lambda_{max}$ of the RNA, to provide a diluted sample solution;

(b) measuring absorbance of the diluted sample solution at lambda maximum of the RNA ($\lambda_{max}$) to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (c) using the Net Absorbance or the adjusted Net Absorbance to determine the RNA concentration in the suspension of the RNA-LNPs.

2. The method of claim 1, wherein the alkylamine comprises a tertiary amine of the formula NRR'R" wherein R, R', and R" are each independently a C1 to C18 alkyl.

3. The method of claim 1, wherein the alkylamine is selected from the group consisting of N,N-dimethylbutylamine (DMBA; CAS 927-62-8), N,N-diethylethanamine (TEA; CAS 121-44-8), N,N-diisopropylethylamine (DIPEA; CAS 7087-68-5), and hexan-1-amine (1-HA; CAS 111-26-2).

4. The method of claim 1, wherein the surfactant is selected from the group consisting of sodium dodecyl sulfate (SDS; CAS 151-21-3), cetyltrimethylammonium bromide (C-TAB; CAS 57-09-0), and polyethylene glycol alkyl ether (BRIJ).

5. The method of claim 1, wherein the surfactant is sodium dodecyl sulfate (SDS) and the alkylamine is N,N-dimethylbutylamine (DMBA) or the surfactant is a polyethylene glycol alkyl ether and the alkylamine is hexan-1-amine (1-HA).

6. The method of claim 1, wherein the ionizable cationic lipids comprise a tertiary amine.

7. The method of claim 6, wherein the ionizable cationic lipid comprises a tertiary amine and at least one saturated or unsaturated hydrocarbon chain comprising at least nine carbon atoms.

8. The method of claim 1, wherein the ionizable cationic lipid is dilinoleylmethyl-4-dimethylaminobutyrate (D-Lin-MC3-DMA; CAS 1224606-06-7).

9. The method of claim 1, wherein the assay diluent further includes a metal chelator.

10. The method of claim 1, wherein the assay diluent comprises about 750 mM N,N-dimethylbutylamine, about 10% (w/v) SDS, and about 1 mM EDTA.

11. The method of claim 1, wherein the RNA concentration is determined using the formula $$mRNA\left(\frac{mg}{mL}\right) = \left(\frac{\text{Net Absorbance or adjusted Net Absorbance}}{\text{path length (cm)}}\right) \times \left(40\ \frac{\mu g \cdot cm}{mL}\right) \times \left(\frac{1\ \frac{mg}{mL}}{1000\ \frac{\mu g}{mL}}\right) \times \text{Dilution Factor}$$

wherein $$\text{Dilution Factor} = \frac{\text{Diluted Sample Solution volume } (\mu L)}{\text{Initial Sample Suspension volume } (\mu L)}.$$

12. A method for measuring the ribonucleic acid (RNA) concentration of a suspension of RNA-lipid nanoparticle (RNA-LNPs), the method comprising:

(a) providing a predetermined volume of a sample suspension comprising RNA-LNPs wherein the RNA-LNPs comprise ionizable cationic lipids and the RNA is at least 100 nucleotides in length;

(b) mixing the sample suspension of RNA-LNPs with a predetermined volume of an assay diluent comprising (i) a surfactant that disrupts the RNA-LNPs into their RNA and LNP components and is optically transparent at $\lambda_{max}$ of the RNA and (ii) an alkylamine that denatures the RNA at a pH of at least pH 11 or about pH 12, displaces the ionizable cationic lipids of the LNP that are associated with or complexed to the denatured RNA, and is optically transparent at $\lambda_{max}$ of the RNA, to provide a diluted sample solution in which the RNA is denatured and dissociated from the ionizable cationic lipids;

(c) measuring absorbance of the diluted sample solution at lambda maximum of the RNA ($\lambda_{max}$) in the diluted sample solution to provide a Net Absorbance or measuring absorbance of the diluted sample solution at $\lambda_{max}$ and at 400 nm and subtracting the absorbance at 400 nm from the absorbance at $\lambda_{max}$ to provide an adjusted Net Absorbance; and (d) using the Net Absorbance or the adjusted Net Absorbance and the formula $$mRNA\left(\frac{\text{mg}}{\text{mL}}\right)=\left(\frac{\text{Net Absorbance or adjusted Net Absorbance}}{\text{path length (cm)}}\right)\times$$

-continued $$\left(40\ \frac{\mu\text{g}\cdot\text{cm}}{\text{mL}}\right)\times\left(\frac{1\ \frac{\text{mg}}{\text{mL}}}{1000\ \frac{\mu\text{g}}{\text{mL}}}\right)\times\text{Dilution Factor}$$

wherein $$\text{Dilution Factor}=\frac{\text{Diluted Sample Solution volume }(\mu\text{L})}{\text{Initial Sample Suspension volume }(\mu\text{L})}$$

to determine the RNA concentration in the suspension of the RNA-LNPs.

13. The method of claim 12, wherein the alkylamine comprises a tertiary amine of the formula NRR'R" wherein R, R', and R" are each independently a C1 to C18 alkyl.

14. The method of claim 12, wherein the surfactant is SDS and the alkylamine is N,N-dimethylbutylamine (DMBA) or the surfactant is a polyethylene glycol alkyl ether and the alkylamine is hexan-1-amine (1-HA).

15. The method of claim 12, wherein the ionizable cationic lipids comprise a tertiary amine.

16. The method of claim 15, wherein the ionizable cationic lipid comprises a tertiary amine and at least one saturated or unsaturated hydrocarbon chain comprising at least nine carbon atoms.

17. The method of claim 12, wherein the ionizable cationic lipid is dilinoleylmethyl-4-dimethylaminobutyrate (D-Lin-MC3-DMA; CAS 1224606-06-7).

18. The method of claim 12, wherein the assay diluent further includes a metal chelator.

19. The method of claim 18, wherein the metal chelator is ethylenediaminetetraacetic acid (EDTA).

20. The method of claim 12, wherein the assay diluent comprises about 750 mM N,N-dimethylbutylamine, about 10% (w/v) SDS, and about 1 mM EDTA.

* * * * *